(12) United States Patent
Hossainy et al.

(10) Patent No.: US 9,517,150 B2
(45) Date of Patent: *Dec. 13, 2016

(54) TIME-DEPENDENT POLYMER SCAFFOLDS

(71) Applicant: Abbott Cardiovascular Systems Inc., Santa Clara, CA (US)

(72) Inventors: Syed Hossainy, Hayward, CA (US); Mikael Trollsas, San Jose, CA (US); Michael Huy Ngo, San Jose, CA (US); Erik David Eli, Redwood City, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/842,432

(22) Filed: Mar. 15, 2013

(65) Prior Publication Data

US 2014/0114398 A1 Apr. 24, 2014

Related U.S. Application Data

(60) Provisional application No. 61/717,613, filed on Oct. 23, 2012.

(51) Int. Cl.
*A61F 2/915* (2013.01)
*A61F 2/958* (2013.01)
(Continued)

(52) U.S. Cl.
CPC .............. *A61F 2/915* (2013.01); *A61F 2/958* (2013.01); *A61L 31/06* (2013.01); *B29C 55/26* (2013.01);
(Continued)

(58) Field of Classification Search
CPC ...... A61F 2/04; A61F 2/82; A61F 2002/9155; A61F 2002/91558; A61F 2002/91566; A61F 2002/91583; A61F 2/915; A61F 2/958; A61F 2002/91575; A61F 2230/0054; A61L 31/06; B29C 55/26; B29C 69/001; B29C 55/24; Y10T 29/49927; Y10T 29/49; B29L 2031/753
See application file for complete search history.

(56) References Cited

U.S. PATENT DOCUMENTS

| | | | |
|---|---|---|---|
| 6,066,167 A | 5/2000 | Lau et al. | |
| 7,985,249 B2 * | 7/2011 | Lowe et al. | 623/1.11 |

(Continued)

FOREIGN PATENT DOCUMENTS

| | | |
|---|---|---|
| EP | 2 016 960 | 1/2009 |
| WO | WO 2010/088776 | 8/2010 |
| WO | WO 2011/094621 | 8/2011 |

OTHER PUBLICATIONS

International Search Report for PCT/US2013/036434, mailed Jul. 29, 2013, 10 pgs.

(Continued)

*Primary Examiner* — Christopher D Prone
*Assistant Examiner* — Rokhaya Diop
(74) *Attorney, Agent, or Firm* — Squire Patton Boggs (US) LLP

(57) ABSTRACT

A medical device includes a polymer scaffold crimped to a catheter having an expansion balloon. The scaffold has a structure that produces a low late lumen loss when implanted within a peripheral vessel and also exhibits a high axial fatigue life. In a preferred embodiment the scaffold forms ring structures interconnected by links, where a ring has 12 crowns and at most two links connecting adjacent rings.

9 Claims, 23 Drawing Sheets

(51) Int. Cl.
  *A61L 31/06*  (2006.01)
  *B29C 69/00*  (2006.01)
  *B29C 55/26*  (2006.01)
  *B29L 31/00*  (2006.01)
  *B29C 55/24*  (2006.01)

(52) U.S. Cl.
  CPC .... *B29C 69/001* (2013.01); *A61F 2002/91575* (2013.01); *A61F 2230/0054* (2013.01); *B29C 55/24* (2013.01); *B29L 2031/753* (2013.01); *Y10T 29/49* (2015.01); *Y10T 29/49927* (2015.01)

(56) References Cited

U.S. PATENT DOCUMENTS

| | | | |
|---|---|---|---|
| 8,414,528 | B2 | 4/2013 | Liu et al. |
| 2003/0050692 | A1 | 3/2003 | Sirhan et al. |
| 2006/0020330 | A1* | 1/2006 | Huang et al. ................ 623/1.49 |
| 2006/0076708 | A1* | 4/2006 | Huang et al. ................ 264/239 |
| 2008/0221661 | A1* | 9/2008 | Bidne et al. ................ 623/1.15 |
| 2008/0275537 | A1 | 11/2008 | Limon |
| 2010/0004735 | A1 | 1/2010 | Yang et al. |
| 2010/0010622 | A1 | 1/2010 | Lowe et al. |
| 2010/0198331 | A1 | 8/2010 | Rapoza et al. |
| 2010/0217377 | A1* | 8/2010 | Tsui ........................ 623/1.15 |
| 2011/0066222 | A1 | 3/2011 | Wang et al. |
| 2011/0066223 | A1 | 3/2011 | Hossainy et al. |
| 2011/0066225 | A1 | 3/2011 | Trollsas et al. |
| 2011/0190871 | A1 | 8/2011 | Trollsas et al. |
| 2011/0190872 | A1* | 8/2011 | Anukhin et al. ............. 623/1.16 |
| 2012/0029618 | A1 | 2/2012 | Tischler et al. |
| 2013/0025110 | A1 | 1/2013 | Stankus et al. |

OTHER PUBLICATIONS

U.S. Appl. No. 13/525,145, filed Jun. 15, 2012, Jayasinghe et al.
U.S. Appl. No. 13/840,257, filed Mar. 15, 2013, Hossainy et al.
Bosiers et al., "Coronary and endovascular applications of the Absorb™ bioresorbable vascular scaffold", Interv. Cardiol. 4(6), pp. 621-631 (2012).
Hademenos et al., "Biophysical Mechanisms of Stroke", Am. Heart Ass. 28, pp. 2067-2077 (1977).
Middleton et al., "Synthetic biodegradable polymers as orthopedic devices", Biomaterials 21, pp. 2335-2346 (2000).

* cited by examiner

| Attribute | FIG.5A | | | | v80 |
|---|---|---|---|---|---|
| | item | in | mm | other | Comments |
| Total Length | – | 1.51 | 38.3 | | Nominal for 40mm balloon, no Marker |
| Number of Rings | – | | | 17 | |
| Number of Links per Ring | – | | | 2 | Evenly distributed |
| Number of Crests per Ring | – | | | 12 | Internal Pattern: U U W U U Y U U W U U Y |
| Cut Tube OD | – | 0.276 | 7.00 | | |
| Wall Thickness | – | 0.011 | 0.279 | | |
| Strut Width | 363a | 0.008 | 0.200 | | |
| Link Width | 363b | 0.008 | 0.200 | | |
| Strut Length | | 0.047 | 1.200 | | |
| Proximal Strut Length | | 0.052 | 1.322 | | Designed for similar theoretical max expansion as body |
| Angle (U) - deg | 368 | | | 81 | Angles based on 7mm tube |
| Angle (W) - deg | 367 | | | 81 | Angles based on 7mm tube |
| Angle (Y) - deg | 366 | | | 81 | Angles based on 7mm tube |
| Inner Radius (U) | 372 | | 0.12 | | |
| Outer Radius (U) | 373 | | 0.32 | | |
| Inner Radius (W) | 372 | | 0.12 | | |
| Outer Radius (W) | 373 | | 0.32 | | |
| Inner Radius (Y) | 372 | | 0.12 | | |

FIG. 6A

| Attribute | FIG.5B | v76 | | |
|---|---|---|---|---|
| | item | in | mm | other |
| Total Length | — | 1.44 | 36.5 | |
| Number of Rings | — | | | 17 |
| Number of Links per Ring | — | | | 2 |
| Number of Crests per Ring | — | | | 8 |
| Cut Tube OD | — | 0.28 | 7 | |
| Wall Thickness | — | 0.011 | 0.279 | |
| Strut Width | 263a | 0.012 | 0.300 | |
| | | | | |
| Link Width | 263b | 0.008 | 0.200 | |
| Strut Length | | 0.069 | 1.740 | |
| | | | | |
| Angle (U) - deg | 268 | | | 81 |
| Angle (W) - deg | 267 | | | 81 |
| Angle (Y) - deg | 266 | | | 81 |
| | | | | |
| Inner Radius (U) | 272 | 0.007 | 0.18 | |
| Outer Radius (U) | 273 | 0.019 | 0.48 | |
| Inner Radius (W) | 272 | 0.007 | 0.18 | |
| Outer Radius (W) | 273 | 0.019 | 0.48 | |
| Inner Radius (Y) | 272 | 0.007 | 0.18 | |

FIG. 6B

| 7% Compression 80,000 cycles @ 1 Hz (1 month) | Axial Compression Tester (Santa Clara) | | |
|---|---|---|---|
| | Fracture @ Crown | Fracture @ Connector Link | Total Fracture |
| V76 (6 x 60 mm) N=5 | 0 ± 0 | 0 ± 0 | 0 ± 0 |

| 7% Compression 500,000 cycles @ 1 Hz (6 months) | Axial Compression Tester (Santa Clara) | | |
|---|---|---|---|
| | Fracture @ Crown | Fracture @ Connector Link | Total Fracture |
| V76 (6 x 60 mm) N=5 | 2.4 ± 2.30 | 2.2 ± 1.92 | 4.6 ± 2.19 |

| Design | Acute Recoil % |
|--------|----------------|
| V59 | 3.2 ± 0.6% |
| V62 | 3.8 ± 0.6% |
| V2 | 2.5 ± 0.5% |
| V76 | 3.3 ± 0.6% |

TIME-DEPENDENT POLYMER SCAFFOLDS

This application claims priority to U.S. Provisional Application No. 61/717,613 filed Oct. 23, 2012. The contents of this provisional application are hereby incorporated by reference in its entirety for all purposes.

FIELD OF THE INVENTION

The present invention relates to bioresorbable scaffolds; more particularly, this invention relates to methods for vascular restorative therapy using a polymeric scaffold.

BACKGROUND OF THE INVENTION

Radially expandable endoprostheses are artificial devices adapted to be implanted in an anatomical lumen. An "anatomical lumen" refers to a cavity, duct, of a tubular organ such as a blood vessel, urinary tract, and bile duct. Stents are examples of endoprostheses that are generally cylindrical in shape and function to hold open and sometimes expand a segment of an anatomical lumen (one example of a stent is found in U.S. Pat. No. 6,066,167 to Lau et al). Stents are often used in the treatment of atherosclerotic stenosis in blood vessels. "Stenosis" refers to a narrowing or constriction of the diameter of a bodily passage or orifice. In such treatments, stents reinforce the walls of the blood vessel and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through an anatomical lumen to a desired treatment site, such as a lesion. "Deployment" corresponds to expansion of the stent within the lumen at the treatment region. Delivery and deployment of a stent are accomplished by positioning the stent about one end of a catheter, inserting the end of the catheter through the skin into an anatomical lumen, advancing the catheter in the anatomical lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon prior to insertion in an anatomical lumen. At the treatment site within the lumen, the stent is expanded by inflating the balloon. The balloon may then be deflated and the catheter withdrawn from the stent and the lumen, leaving the stent at the treatment site. In the case of a self-expanding stent, the stent may be secured to the catheter via a retractable sheath. When the stent is at the treatment site, the sheath may be withdrawn which allows the stent to self-expand.

The stent must be able to satisfy a number of basic, functional requirements. The stent must be capable of withstanding the structural loads, for example, radial compressive forces, imposed on the stent as it supports the walls of a vessel after deployment. Therefore, a stent must possess adequate radial strength. After deployment, the stent must adequately maintain its size and shape throughout its service life despite the various forces that may come to bear on it. In particular, the stent must adequately maintain a vessel at a prescribed diameter for a desired treatment time despite these forces. The treatment time may correspond to the time required for the vessel walls to remodel, after which the stent is no longer necessary for the vessel to maintain a desired diameter.

Radial strength, which is the ability of a stent to resist radial compressive forces, relates to a stent's radial yield strength around a circumferential direction of the stent. A stent's "radial yield strength" or "radial strength" (for purposes of this application) may be understood as the compressive loading, which if exceeded, creates a yield stress condition resulting in the stent diameter not returning to its unloaded diameter, i.e., there is irrecoverable deformation of the stent. When the radial yield strength is exceeded the stent is expected to yield more severely and only a minimal force is required to cause major deformation.

Even before the radial yield strength is exceeded there may be permanent deformation in the stent a following radial compressive load, but this degree of permanent deformation somewhere in the stent is not severe enough to have a significant effect on the stent's overall ability to radially support a vessel. Therefore, in some cases the art may view "radial yield strength" as the maximum radial loading, beyond which the scaffold stiffness changes dramatically. "Radial yield strength" units are sometimes force-divided-by-length, which is an expression of radial yield strength on a per-unit-length basis. Thus, for a radial yield strength per unit length, e.g., F N/mm, the radial load which, if it exceeds this value, would result in significant change in stiffness for a stent having two different lengths, L1 and L2, would therefore be the product F*L1 and F*L2, respectively. The value F, however, is the same in both cases, so that a convenient expression can be used to appreciate the radial yield strength independent of the length of the stent. Typically, the radial force that identifies the point where stiffness is lost does not change much on a per-unit-length basis when the stent length changes.

A radial "stiffness" refers to the amount net radial inward force (i.e., uniform radial inward pressure over the entire abluminal scaffold surface x the abluminal surface area) required to reversibly decrease a scaffold diameter by a certain amount. The slope of the curve from a force-deflection plot will be called the "absolute stiffness" or K. The units are N/mm and the stiffness is expressed for the linearly elastic range of response to the radial force. Thus, for a scaffold deployed to 6.5 mm and having a linear elastic range for radial compression between 6.5 mm and 5.5 mm and a radial stiffness of 20 N/mm, a net inward radial inward force of 10 N is needed to decrease the scaffold diameter from 6.5 mm to 6.0 mm. After the radial force is removed, the scaffold returns to the 6.5 mm diameter.

Alternatively, scaffold radial stiffness may be expressed as a stiffness normalized to the scaffold length, or "length-normalized stiffness" (K-Lnorm). First, the radial deflection is measured for an applied force. Next, for each recorded change in scaffold length, the corresponding applied force is divided by the length of the scaffold. This normalized force (e.g., N/mm) is then used with the displacements to compute a stiffness, rather than the actual force that produced the displacement. The resulting length-normalized stiffness has units of (N/mm per mm). The relationship between K and K-Lnorm for a scaffold with length L is $$K\text{-}Lnorm = [(F2/L - F1/L) * (D2 - D1)^{-1}]$$
$$= (1/L) * [(F2 - F1) * (D2 - D1)^{-1}]$$
$$= (1/L) * K$$

Where D2 is the measured scaffold diameter when uniform radial force F2 is applied and D1 is the measured scaffold diameter when uniform radial force F1 is applied. Hence, K is obtained by multiplying K-Lnorm by the scaffold length L.

Alternatively, scaffold radial stiffness may be normalized both with respect to the scaffold length (L) and the scaffold initial diameter (Do), or "Intrinsic stiffness" (K-norm). The relationships among the three types of radial stiffness are $$K\text{-norm}=(Do)*K\text{-Lnorm}=(Do/L)*K$$

Similar definitions are adopted for a pinching stiffness, which may be measured by a flat-plate test. Pinching stiffness is discussed in US20110190871. Thus, an absolute, length normalized and intrinsic pinching stiffness, denoted as KP, KP-Lnorm and KP-norm, respectively, for a scaffold of length L and initial height (diameter) Do are $$KP\text{-norm}=(Do)*KP\text{-Lnorm}=(Do/L)*KP$$

A commonly used type of peripheral stent is the self-expanding stent made from super-elastic material, such as Nitinol. This type of material is known for its ability to return to its original configuration after severe deformation, such as a crushing load or longitudinal bending. However, this variety of self-expanding stents have undesired qualities; most notably, the high resiliency of super-elastic material produces what is commonly referred to as a "chronic outward force" (COF) on the blood vessel supported by the stent. Complications resulting from COF are discussed in Schwartz, Lewis B. et al. *Does Stent Placement have a learning curve: what mistakes do we as operators have to make and how can they be avoided?*, Abbott Laboratories; Abbott Park, Ill., USA. It is believed that a COF exerted on a blood vessel by a self-expending stent is a main contributor to high degrees of restenosis of lesions treated by the self-expanding stent. It has been shown that not even an anti-proliferative drug delivered from drug eluting self-expandable stents can mitigate the restenosis caused by the stent's COF. Stents that are plastically deformed by a balloon to support a vessel do not suffer from this drawback. Indeed, balloon expanded stents, in contrast to self-expanding stents made from a super-elastic material, have the desirable quality of being deployable to the desired diameter for supporting the vessel without exerting residual outward forces on the vessel.

A balloon-expanded polymer scaffold, such as that described in US 2010/0004735 is made from a biodegradable, bioabsorbable, bioresorbable, or bioerodible polymer. The terms biodegradable, bioabsorbable, bioresorbable, bio-soluble or bioerodible refer to the property of a material or stent to degrade, absorb, resorb, or erode away from an implant site. The polymer scaffold described in US 2010/0004735, for example, as opposed to a metal stent, is intended to remain in the body for only a limited period of time. In many treatment applications, the presence of a stent in a body may be necessary for a limited period of time until its intended function of, for example, maintaining vascular patency and/or drug delivery is accomplished. Moreover, it has been shown that biodegradable scaffolds allow for improved healing of the anatomical lumen as compared to metal stents, which may lead to a reduced incidence of late stage thrombosis. In these cases, there is a desire to treat a vessel using a polymer scaffold, in particular a bioerodible polymer scaffold, as opposed to a metal stent, so that the prosthesis's presence in the vessel is for a limited duration. However, there are numerous challenges to overcome when developing a polymer scaffold.

The art recognizes a variety of factors that affect a polymeric scaffold's ability to retain its structural integrity and/or shape when subjected to external loadings, such as crimping and balloon expansion forces. These interactions are complex and the mechanisms of action not fully understood. According to the art, characteristics differentiating a polymeric, bio-absorbable scaffold of the type expanded to a deployed state by plastic deformation from a similarly functioning metal scaffold are many and significant. Indeed, several of the accepted analytic or empirical methods/models used to predict the behavior of metallic scaffolds tend to be unreliable, if not inappropriate, as methods/models for reliably and consistently predicting the highly non-linear, time dependent behavior of a polymeric load-bearing structure of a balloon-expandable scaffold. The models are not generally capable of providing an acceptable degree of certainty required for purposes of implanting the scaffold within a body, or predicting/anticipating the empirical data.

Polymer material considered for use as a polymeric scaffold, e.g. poly(L-lactide) ("PLLA"), poly(L-lactide-co-glycolide) ("PLGA"), poly(D-lactide-co-glycolide) or poly(L-lactide-co-D-lactide) ("PLLA-co-PDLA") with less than 10% D-lactide, and PLLD/PDLA stereo complex, may be described, through comparison with a metallic material used to form a stent, in some of the following ways. A suitable polymer has a low strength to weight ratio, which means more material is needed to provide an equivalent mechanical property to that of a metal. Therefore, struts must be made thicker and wider to have the required strength for a stent to support lumen walls at a desired radius. The scaffold made from such polymers also tends to be brittle or have limited fracture toughness. The anisotropic and rate-dependant inelastic properties (i.e., strength/stiffness of the material varies depending upon the rate at which the material is deformed) inherent in the material, only compound this complexity in working with a polymer, particularly, bio-absorbable polymer such as PLLA or PLGA.

Processing steps performed on, and design changes made to a metal stent that have not typically raised concerns for, or required careful attention to unanticipated changes in the average mechanical properties of the material, therefore, may not also apply to a polymer scaffold due to the non-linear and sometimes unpredictable nature of the mechanical properties of the polymer under a similar loading condition. It is sometimes the case that one needs to undertake extensive validation before it even becomes possible to predict more generally whether a particular condition is due to one factor or another—e.g., was a defect the result of one or more steps of a fabrication process, or one or more steps in a process that takes place after scaffold fabrication, e.g., crimping? As a consequence, a change to a fabrication process, post-fabrication process or even relatively minor changes to a scaffold pattern design must, generally speaking, be investigated more thoroughly than if a metallic material were used instead of the polymer. It follows, therefore, that when choosing among different polymeric scaffold designs for improvement thereof, there are far less inferences, theories, or systematic methods of discovery available, as a tool for steering one clear of unproductive paths, and towards more productive paths for improvement, than when making changes in a metal stent.

The present inventors recognize, therefore, that, whereas inferences previously accepted in the art for stent validation or feasibility when an isotropic and ductile metallic material was used, those inferences would be inappropriate for a polymeric scaffold. A change in a polymeric scaffold pattern may affect not only the stiffness or lumen coverage of the scaffold in its deployed state supporting a lumen, but also the propensity for fractures to develop when the scaffold is crimped or being deployed. This means that, in comparison to a metallic stent, there is generally no assumption that can be made as to whether a changed scaffold pattern may not produce an adverse outcome, or require a significant change in a processing step (e.g., tube forming, laser cutting, crimping, etc.). Simply put, the highly favorable, inherent properties of a metal (generally invariant stress/strain properties with respect to the rate of deformation or the direction of loading, and the material's ductile nature), which simplify the stent fabrication process, allow for inferences to be more easily drawn between a changed stent pattern and/or a processing step and the ability for the stent to be reliably manufactured with the new pattern and without defects when implanted within a living being.

A change in the pattern of the struts and rings of a polymeric scaffold that is plastically deformed, both when crimped to, and when later deployed by a balloon, unfortunately, is not predictable to the same or similar degree as for a metal stent. Indeed, it is recognized that unexpected problems may arise in polymer scaffold fabrication steps as a result of a changed pattern that would not have necessitated any changes if the pattern was instead formed from a metal tube. In contrast to changes in a metallic stent pattern, a change in polymer scaffold pattern may necessitate other modifications in fabrication steps or post-fabrication processing, such as crimping and sterilization.

Scaffolds used to treat coronary vessels experience, for the most part, a primarily radial loading. However, scaffolds intended for peripheral vessels experience a quite different loading, to such an extent that the traditional measure of a stent's fitness for use, i.e., its radial strength/stiffness, is not an accurate measure of whether the scaffold will have sufficient strength to provide mechanical support within the peripheral vessel for the duration needed. This is because a peripheral scaffold is placed in a significantly different environment from a coronary scaffold. The vessel size is larger. And there is much more movement of the vessel, especially when located close to an appendage. As such, a scaffold intended for a peripheral vessel will need to be able to sustain more complex loading, including a combination of axial, bending, torsional and radial loading. See e.g. Bosiers, M. and Schwartz, L., *Development of Bioresorbable Scaffolds for the Superficial Femoral Artery*, SFA: CONTEMPORARY ENDOVASCULAR MANAGEMENT ("Interventions in the SFA" section). These and related challenges facing peripherally implanted stents and scaffolds are also discussed in U.S. application Ser. No. 13/015,474.

There is a need to develop a prosthesis for treating peripheral blood vessels that can maintain its structural integrity for a period of time long enough to provide a mechanical support for the vessel, until this support is no longer needed. There is a further need to develop such a prosthesis that minimizes late lumen loss and stenosis of the vessel, such as within the first month following implantation, thereby providing improved vascular patency.

SUMMARY OF THE INVENTION

There is a need to develop a system for vascular restorative therapy incorporating principles of scaffold modulation of a vessel site over time, as the vessel heals and providing a platform for tissue engineering at the implant site.

According to one aspect of the invention, a medical device includes a balloon-expanded scaffold formed from a radially expanded polymer tube, the scaffold forming a network of rings interconnected by links including (1) at least 8 crests per ring and no more than 2 links connecting a pair of adjacent rings, or (2) at least 12 crests per ring; and wherein the scaffold radial stiffness relative to a pre-implant stiffness for the period of initial implantation until 3 months following implantation, $S(t)/S_o$, $t=0 \ldots 90$ days or 180 days, satisfies:

$$S/S_o = S_{ov}/S_o + (1 - S_{ov}/S_o - C)e^{-t/k} + Ce^{-t/K_o},$$

wherein t is time (days),

So is the radial strength/stiffness of the scaffold prior to implantation;

Sov is the approximate radial strength/stiffness of the native vessel;

Ko, C are parameters reflecting an initial rise in stiffness; and

K is a time constant reflecting a decrease in stiffness over a patency period.

According to another aspect of the invention, upon implantation and within two weeks following implantation in a vessel the radial strength or stiffness of the scaffold increases by 60% and from about the approximately two week after implantation until about three months after implantation the radial strength/stiffness decreases up to 50% of the scaffold's pre-implant strength/stiffness.

According to another aspect of the invention, upon implantation and up to about three months after implantation the radial strength/stiffness of the scaffold decreases by up to 20%, between 10-20% or between 20-30%.

According to another aspect of the invention, the scaffold's radial strength prior to implantation is between 0.4 N/mm and 0.75 N/mm and a rise in the scaffold's radial strength following implantation is 0.8 N/mm and 1.2 N/mm.

According to another aspect of the invention a ratio of S/SO is 1 to 1.3 to 1.5, 1.5 to 2.25, or 1.5 to 2.0 where S is pinching strength/stiffness or radial strength/stiffness.

According to another aspect a scaffold has no strut discontinuities, or less than about 5, 7, 10, 15, or 20 percent strut discontinuities when subjected to a six month simulated walking test.

According to another aspect of the invention, a slope or rate of change in a mechanical property of a peripheral scaffold with respect to time over the interval of greater than about 7 days and up to 3 months from implantation may range from about −1 to −0.37, more narrowly, about −0.5 to −0.3, and about −0.8 to −0.2. In some embodiments, the slope may be, for between 7-28 days between about −0.55 and −0.45, and −1 to −0.8. The slope may be, in some embodiments, for between 28 and 60 days between about −0.45 and −0.35, or −0.55 to −0.35. All of the above slope value ranges may be present in a scaffold structure made from a polymer composition comprising PLLA, have rings connected by link elements and a ring may have 8 to 12 crests and 8 to 12 troughs, respectively, 8 crests and 8 troughs, 12 crests and 12 troughs, and at most 2 links, or at most 3 links. All of the foregoing slopes, apply to ranges of 1-3 months, 1 month, 2 months, or a slope over a day (TABLE 1.5) are within the scope of the invention.

In accordance with the foregoing, there is also provided a peripherally-implantable and bio-erodible polymer scaffold that has a lower fracture rate, discontinuity or percentage of fractured structure. The scaffold is capable of maintaining its scaffolding support of a vessel wall sufficiently for up to about a 1, 2, and 3 month period following implantation, following which the scaffolding begins to degrade as it should no longer be needed to maintain vascular patency. Surprisingly and unexpectedly, the polymer scaffold according to one embodiment is capable of producing a significantly lower late lumen loss than prior scaffold designs about 28 days after implantation.

According to one aspect of the invention, there is a balloon-expandable scaffold forming ring structures. Each ring is connected to adjacent rings by no more than two links and each ring has at least 8 crests and 8 troughs, and preferably 12 crests and 12 troughs formed by strut elements. The high number of crowns in the preferred embodiment is believed to provide a higher density of strut elements to support the vessel such that the surface area provided to support the vessel increases over a scaffold having fewer crowns. Additionally, for the same number of cracks or fractures occurring in the scaffold (as compared to a scaffold having fewer crowns) the overall percentage of cracks at crowns is reduced. Additionally, a higher number of crowns increase the axial flexibility of the scaffold by creating an additional unattached crown on either side of the link. This unattached crown (i.e. a "u" rather than "y" or "w" crest) creates a more flexible section between links. This reduces the force required to axial compress the stent and thus reduces the stress concentrations during axial compression. It is believed that the combination of increased supporting surface area for the vessel walls, reduced stress concentrations by increased crowns and lower percentage of cracked to un-cracked or functional crowns is a significant factor contributing to a reduction in late lumen loss and reduced stenosis of the vessel.

According to another aspect of the invention, a scaffold provides a desired vascular patency by increasing the surface area coverage of a scaffold at the expense of reducing the radial strength of the scaffold. In one example, a scaffold pattern is characterized by a reduced strut length and increased number of crowns for ring structures. For this scaffold an equal number of fractures as a more radial-stiff scaffold produces a lower percentage of functioning-to-nonfunctioning crown-strut structures due to a higher number of such structures as compared to the more radial stiff scaffold.

According to another aspect of the invention, there is provided a scaffold having at most two links, or no more than three links connecting adjacent ring structure and with or without an increased number of crowns to extend the scaffold's fatigue life during the period of time when the scaffold is needed to provide mechanical support to the vessel, e.g., during the first about one, two or three months following implantation. Tests have revealed that for a peripherally-implanted scaffold, particularly for scaffold located within arteries of appendages, failure in the scaffold structure has most often occurred due to repeated axial compression/extension and bending. Although the scaffold is in general subjected to a complex and time-varying combination of radial, axial, bending and torsion loads, it has been found that prior scaffold designs have been mostly susceptible to crack formation due to repeated cyclic axial and bending loads, e.g., 500,000 cycles of 7% axial compression/extension, which is considered equivalent to walking over a six month period. Repeated impacts between ring structures, longitudinal buckling (bending) of links or other behavior that may result from a reduction of axial and bending stiffness were not found to have a significant negative impact on vessel support or scaffold integrity based on in-vivo studies.

As an example of bending-induced fractures, an earlier design—the V59, which is described in WO2011094621—showed by comparison many more fractures during bending fatigue tests (90 degree bending at 1 Hz under water at 37 Deg. Celsius) up to 1.7 million cycles. The cause for these failures was the scaffold being too stiff in bending, or its fracture toughness in bending not adequate for the test loading environment. The V59 has four links connecting adjacent ring structures. When a two link design is used, e.g., the V76 or V80, the same testing revealed substantially less fractures.

Again, the actual in-vivo loading environment is quite complex, involving axial, bending, torsion and radial loads. However, it was revealed through separate bending and axial loading bench tests for a four link verses a two link design compared to in-vivo data that when both bending and axial loading induced fractures were reduced in the bench tests, the fracture count of explanted scaffolds was also reduced significantly for the two verses four link scaffolds. This indicates that it is not so much the radial loading, but other loading not typically associated with critical stent mechanical functioning that is a key driver for balloon-expandable and peripherally-implantable scaffold design.

According to one embodiment, a peripherally-implanted medical device includes a balloon-expanded scaffold formed from a radially expanded polymer tube, the scaffold forming a network of rings interconnected by links, including at least 8 crests and 8 troughs per ring, or 12 crests and 12 troughs per ring, and at most 2 links connecting substantially all pairs of adjacent rings, wherein for any ring of the scaffold there are an equal number of unsupported crowns on each side of each crown connected to a link. The two links allows the structure to better absorb/distribute stresses induced during combined axial loading and bending. Moreover, it was found that the structure's overall fatigue life is significantly increased when two links are used. Additionally, symmetry of the crowns about a link helps to more equally distribute stresses, or reduce stress concentrations near crowns to improve fatigue life during axial loading and bending. Symmetry in the number of crowns on either side of links provides for symmetric loading in the link at both proximal and distal connection points. An asymmetric design, which means having more crowns/crests on one side of a link than the other side, creates an asymmetric loading on a ring such as twisting or out of plane bending moments, which shortens the fatigue life of the design in axial and bending fatigue.

According to one aspect of the invention a peripherally-implanted medical device comprises a balloon-expanded scaffold formed from a biaxially expanded polymer tube; the scaffold forming a network of rings interconnected by links, including 8 crests and 8 troughs per ring, or 12 crests and 12 troughs per ring, and at most 2 links connecting substantially all pairs of adjacent rings, wherein for any ring of the scaffold there are an equal number of unsupported crowns on each side of each crown connected to a link; wherein after being submerged in water at 37 Deg. C for 6-7 days a mechanical property of the scaffold increases by between about 1.2 and 2.0.

The device may include one or more of the following features either separately or together in any combination: wherein the material property is radial stiffness and the scaffold has an intrinsic stiffness (K-norm) of between about 15 and 7, or 12 and 8, or 12-10, or greater than 8; wherein the scaffold has a crush recovery such that attains over 80% of its post-dilation diameter after being crushed to 50% of its post-dilation diameter; wherein the scaffold is crimped to a balloon, and the scaffold has a crimped diameter that is at least 2.5 times less than the balloon nominal inflation diameter; and/or wherein the scaffold is formed from a biaxially expanded tube comprising PLLA.

According to one aspect of the invention a peripherally-implanted medical device comprises a balloon-expanded scaffold formed from a biaxially expanded polymer tube; the scaffold forming a network of rings interconnected by links, including 8 crests and 8 troughs per ring, or 12 crests and 12 troughs per ring, and at most 2 links connecting substantially all pairs of adjacent rings, wherein for any ring of the scaffold there are an equal number of unsupported crowns on each side of each crown connected to a link; wherein the scaffold has a material property; and wherein following a six month simulated walking test the material property is the same as, or decreases by about 5%, 8%, 10%, 15% or 20%.

The device may include one or more of the following features either separately or together in any combination: wherein the material property is at least one of the percent of intact struts, radial stiffness (K, K-norm or K-Lnorm), crush recovery energy, and radial strength; wherein the scaffold is formed from a polymer tube having a semicrystalline structure resulting from a process where an extruded polymer tube is radially expanded using a radial draw ratio of about 400% to produce the radially expanded tube having an average crystal size after radial expansion of less than about 10 microns; where the polymer is PLLA; wherein the scaffold is crimped to a 6 mm delivery balloon and is cut from a biaxially-expanded tube having at least a 7 mm outer diameter; wherein the scaffold has an intrinsic stiffness (K-norm) of between about 15 and 7, or 12 and 8, or 12-10, or greater than 8 and a crush recovery such that it attains at least 90%, or at least 80% of its diameter after being crushed to at most 50% of its diameter; wherein the scaffold is cut from a tube having a ratio of tube diameter to wall thickness of between about 25-30; wherein the scaffold is crimped to a balloon, the crimped scaffold material having a morphology characterized by (1) substantially radially aligned polymer chains resulting from a biaxial expansion of the scaffold in the radial direction by between 300 to 400% of a pre-expansion tube diameter, and (2) the scaffold is crimped from a starting or pre-crimp diameter to a diameter that is at least 2-3 times reduced from its starting diameter; wherein the scaffold is made from a polymer composition comprising PLLA; wherein the scaffold forms crown angles of about 80 degrees before crimping and when crimped the crown angles are less than 10 degrees, or less than 5 degrees, or about zero degrees; and/or wherein the polymer chains of the crimped scaffold are aligned substantially in a radial direction resulting from a radial expansion percentage of between about 400% and 450% and axial expansion of between 10% and 50%. A radial expansion may also be between 400-500% and the axial expansion may be 150-200%, and a radial to axial expansion of 400/200 or 200/200.

According to one aspect of the invention a peripherally-implanted medical device comprises a balloon-expanded scaffold formed from a radially expanded polymer tube; the scaffold forming a network of rings interconnected by links, including at least 8 crests per ring, and at most 2 links connecting substantially all pairs of adjacent rings, wherein for any ring of the scaffold there are an equal number of unsupported crowns on each side of each crown connected to a link; and wherein the scaffold attains over 80% of its diameter after being crushed to over 50% of its expanded diameter. The device may include one or more of the following features either separately or together in any combination: wherein the scaffold attains about 80% of its diameter after being crushed to over 60% of its expanded diameter; wherein the scaffold has a length of at least 30 mm, 40 mm and between 50 and up to 100 mm; and/or wherein the scaffold has at least 90% of its struts intact after a six-month simulated walking test.

According to one aspect of the invention a medical device comprises a balloon-expanded scaffold formed from a radially expanded polymer tube, the scaffold forming a network of rings interconnected by links including (1) at least 8 crests per ring and no more than 3 links connecting a pair of adjacent rings, or (2) at least 12 crests per ring; wherein the scaffold has a post-implant mechanical property S(t) relative to the mechanical property pre-implant So; and wherein S(t)/So from the period of initial implantation until 3 months following implantation, S(t)/So, t=0 . . . 90 days, satisfies:

$$S/So = Sov/So + (1 - Sov/So - C)e^{-t/k} + Ce^{-t/Ko}$$

wherein t is time (days),
So is a mechanical property prior to implantation;
Sov is the approximate radial or pinching strength/stiffness of the native vessel;
Ko, C are parameters reflecting an initial rise in strength/stiffness, where $C = R/(S0*(1/K - 1/K0))$; and
K is a time constant reflecting a decrease in strength/stiffness over a patency period; and
wherein Ko, C, K, and R/So are for either SCAFFOLD1 or SCAFFOLD2 types:

|  | SCAFFOLD1 | SCAFFOLD2 |
| --- | --- | --- |
| Ko (days) | 0.45–0.6 | 0.45–2.5 |
| C | 0.66–2.0 | 0.66–7.0 |
| K (days) | 200-375 | 70-1000 |
| R/So | (−0.3) to (−1.2) | (−0.275) to (−2.5) |

The device may include one or more of the following features either separately or together in any combination: wherein the quantity $100*d(S(t)/S_o)/dt$ over the interval of 7 days to 28 days following implantation is about −1 to −0.5; wherein the quantity $S(t=7\ days)/S_o$ is between 1.0 and 2.5, or between 1.1 and 1.3; or between about 0.9 and 2.25; wherein the quantity $S(t=28\ days)/S_o$ is less than $S(t=7\ days)/S_o$ and between 1.0 and 1.3; wherein the quantity $S(t=60\ days)/S_o$ is less than $S(t=28\ days)/S_o$ and between about 0.7 and 1; wherein the quantity $S(t=90\ days)/S_o$ is less than $S(t=60\ days)/S_o$ and between about 0.7 and 0.9; wherein S(t) and So are post and pre implant pinching stiffness for the scaffold, respectively; a method for making the medical device having the properties described above, comprising making a scaffold from a radially-expanded tube; and/or a method of assembling a medical device having the properties described above, comprising crimping a scaffold to a balloon, including the steps of radially reducing the scaffold diameter by at least 200% while the scaffold has a temperature of between 5-15 degrees below Tg-LOW.

According to one aspect of the invention a method for vascular restorative therapy of a peripheral vessel comprises making a scaffold comprising forming a polymer tube and forming the scaffold form the polymer tube; and crimping the scaffold to a balloon; whereupon implantation of the scaffold in the peripheral vessel by inflation of the balloon the scaffold has the following characteristics: between about 8-15% fractured struts after 28 days; K-norm is between about 7 and 15; the scaffold expanded diameter is greater than 5 mm; the scaffold has a ratio of wall thickness to diameter of about 20-40; and the scaffold has a length greater than 40 mm.

According to another embodiment, a medical device includes a balloon-expanded scaffold formed from a radially expanded polymer tube, the scaffold forming a network of rings interconnected by links including (1) at least 8 crests per ring and no more than 2 links connecting a pair of adjacent rings, or (2) at least 12 crests per ring; wherein upon implantation and within two weeks following implantation in a vessel the radial strength or stiffness of the scaffold increases by 60%; and wherein from about the approximately two week after implantation until about three months after implantation the radial or pinching strength/stiffness decreases up to 10%-50% of the scaffold's pre-implant strength/stiffness either in-vivo or for a six month simulated walking test.

According to another aspect of invention a peripheral vessel comprises making a scaffold formed from a tube having a morphology comprising biaxially aligned chains of 400/200 or 200/200, the scaffold being in a pre-crimp condition or crimped to a balloon; whereupon inflation of the scaffold the scaffold has the following characteristics: between about 8-15% fractured struts after 28 days in-vivo or after six-month simulated walking test; K-norm is between about 7 and 15; the scaffold expanded diameter is greater than 5 mm; the scaffold has a ratio of diameter to wall thickness of about 25-30; and the scaffold has a length greater than 40 mm.

According to another embodiment, there is a method for treatment of a vessel using vascular restoration therapy. This method according to the invention may be described in the following manner:

designing a bioresorbable scaffold that changes its load-bearing mechanical property as a function of time commensurate with the loading condition of the implant site (coronary or peripheral);
wherein as a result of the implant's time-varying properties,
there is a reduction of trauma to the implant site caused by the implant.
the scaffold produces mechanical conditioning in combination with a tissue engineering template property, to improve a diseased vessel's function and hemodynamic response close to a healthy native vessel's values; and
hemodynamic and functional values farther downstream of the implant improve close to healthy physiological values.

Mechanical conditioning: gradual loss as a f(t) of mechanical property of an implant, such as stiffness, modulus, moment of inertia, reducing different mode of implant-induced stresses on the vessel and restriction of vessel micro-motion at or near the implant site.

Tissue engineering (TE) template: An implant that enhances cellular conduction and ingrowth into the implant by physical morphology features such as texture, porosity, structural dimension and, optionally, can produce agents to induce cellular ingrowth by chemical interaction with the cells.

Loading condition: intensity and the nature of a load experienced by an implant. This includes point load, distributed load, cyclic load, transient load, load amplitude, load frequency. For example, Coronary loading condition has minimal extraneous perturbation forces while SFA peripheral vessel experiences significant external forces.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

BRIEF DESCRIPTION OF THE DRAWINGS

FIGS. 6A and 6B are tables showing examples of scaffold features in accordance with aspects of the disclosure.

DETAILED DESCRIPTION OF EMBODIMENTS

Figure 1:
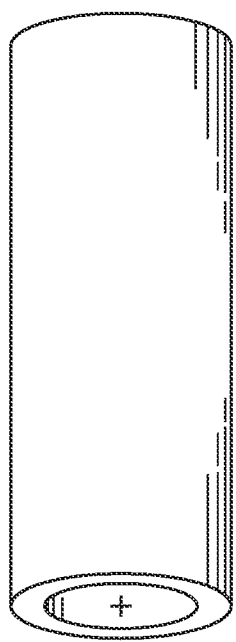
FIG. 1 is a perspective view of a deformed polymer tube. The tube is formed into a scaffold.

The disclosure provides examples of parameters and characteristics of scaffolds useful as design criterion for promoting favorable vascular restorative therapy (VRT). According to the disclosure there are examples applied specifically to a peripherally-implanted, bioresorbable scaffold. The concepts disclosed, however, are useful for a wider variety of luminal indication such as coronary, intracranial vessels, carotid vessels, venous location such as AV fistula, IVC, airway obstruction, tracheal implant, biliary implant etc.

For purposes of this disclosure, the following terms and definitions apply:

The term "about" means 10%, 5%, or 2% less or more than a stated value, a range or each endpoint of a stated range, or a one-sigma variation from a stated mean value.

"Reference vessel diameter" (RVD) is the diameter of a vessel in areas adjacent to a diseased section of a vessel that appear either normal or only minimally diseased.

"Minimal lumen diameter" (MLD) is the diameter of a diseased section of a vessel at the site of maximal reduction in the diameter.

% "Diameter restenosis" (% DS) is the percent difference between the reference vessel diameter and the minimal lumen diameter: (RVD−MLD)/RVD "Acute gain" is defined as the difference between pre- and post-procedural minimal lumen diameter.

"Late loss" is defined as the difference between minimal luminal diameter after the procedure or post-percutaneous coronary intervention (PCI) and minimal luminal diameter at follow-up.

"Inflated diameter" or "expanded diameter" refers to the diameter the scaffold attains when its supporting balloon is inflated to expand the scaffold from its crimped configuration to implant the scaffold within a vessel. The inflated diameter may refer to a post-dilation balloon diameter which is beyond the nominal balloon diameter, e.g., a 6.5 mm balloon has about a 7.4 mm post-dilation diameter, or a 6.0 mm balloon has about a 6.5 mm post-dilation diameter. The nominal to post dilation ratios for a balloon may range from 1.05 to 1.15 (i.e., a post-dilation diameter may be 5% to 15% greater than a nominal inflated balloon diameter). The scaffold diameter, after attaining an inflated diameter by balloon pressure, will to some degree decrease in diameter due to recoil effects related primarily to, any or all of, the manner in which the scaffold was fabricated and processed, the scaffold material and the scaffold design.

"Post-dilation diameter" (PDD) of a scaffold refers to the diameter of the scaffold after being increased to its expanded diameter and the balloon removed from the patient's vasculature. The PDD accounts for the effects of recoil. For example, an acute PDD refers to the scaffold diameter that accounts for an acute recoil in the scaffold.

A "pre-crimp diameter" means an OD of a tube, or the scaffold before it is crimped to a balloon. Similarly, a "crimped diameter" means the OD of the scaffold when crimped to a balloon. The "pre-crimp diameter" can be 2, 2.5, 3.0 times greater than the crimped diameter and about 0.9, 1.0, 1.1, 1.3 and about 1-1.5 times higher than an expanded diameter or post-dilation diameter.

"Recoil" means the response of a material following the plastic/inelastic deformation of the material. When the scaffold is radially deformed well beyond its elastic range and the external pressure (e.g., a balloon pressure on the luminal surface) is removed the scaffold diameter will tend to revert back to its earlier state before the external pressure was applied. Thus, when a scaffold is radially expanded by applied balloon pressure and the balloon removed, the scaffold will tend to return towards the smaller diameter it had, i.e., crimped diameter, before balloon pressure was applied. A scaffold that has recoil of 10% within ½ hour following implantation and an expanded diameter of 6 mm has an acute post-dilation diameter of 5.4 mm. The recoil effect for balloon-expanded scaffolds can occur over a long period of time. Post-implant inspection of scaffolds shows that recoil can increase over a period of about one week following implantation. Unless stated otherwise, when reference is made to "recoil" it is meant to mean recoil along a radial direction (as opposed to axial or along longitudinal direction) of the scaffold.

"Acute Recoil" is defined as the percentage decrease in scaffold diameter within the first about ½ hour following implantation within a vessel.

The glass transition temperature (referred to herein as "Tg") is the temperature at which the amorphous domains of a polymer change from a brittle vitreous state to a solid deformable or ductile state at atmospheric pressure. In other words, Tg corresponds to the temperature where the onset of segmental motion in the chains of the polymer occurs. Tg of a given polymer can be dependent on the heating rate and can be influenced by the thermal history of the polymer. Furthermore, the chemical structure of the polymer heavily influences the glass transition by affecting mobility of polymer chains. A lower end of Tg is Tg-LOW, a midpoint is Tg-MID and upper end is Tg-HIGH.

"Stress" refers to force per unit area, as in the force acting through a small area within a plane within a subject material. Stress can be divided into components, normal and parallel to the plane, called normal stress and shear stress, respectively. Tensile stress, for example, is a normal component of stress that leads to expansion (increase in length) of the subject material. In addition, compressive stress is a normal component of stress resulting in compaction (decrease in length) of the subject material.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Modulus" may be defined as the ratio of a component of stress or force per unit area applied to a material divided by the strain along an axis of applied force that result from the applied force. For example, a material has both a tensile and a compressive modulus.

"Toughness", or "fracture toughness" is the amount of energy absorbed prior to fracture, or equivalently, the amount of work required to fracture a material. One measure of toughness is the area under a stress-strain curve from zero strain to the strain at fracture. The stress is proportional to the tensile force on the material and the strain is proportional to its length. The area under the curve then is proportional to the integral of the force over the distance the polymer stretches before breaking. This integral is the work (energy) required to break the sample. The toughness is a measure of the energy a sample can absorb before it breaks. There is a difference between toughness and strength. A material that is strong, but not tough is said to be brittle. Brittle materials are strong, but cannot deform very much before breaking.

As used herein, the terms "axial" and "longitudinal" are used interchangeably and refer to a direction, orientation, or line that is parallel or substantially parallel to the central axis of a stent or the central axis of a tubular construct. The term "circumferential" refers to the direction along a circumference of the stent or tubular construct. The term "radial" refers to a direction, orientation, or line that is perpendicular or substantially perpendicular to the central axis of the stent or the central axis of a tubular construct and is sometimes used to describe a circumferential property, i.e radial strength.

The term "crush recovery" is used to describe how the scaffold recovers from a pinch or crush load, while the term "crush resistance" is used to describe the force required to cause a permanent deformation of a scaffold. A scaffold or stent that does not possess good crush recovery does not substantially return to its original diameter following removal of a crushing force. As noted earlier, a scaffold or stent having a desired radial force can have an unacceptable crush recovery. And a scaffold or stent having a desired crush recovery can have an unacceptable radial force. Crush recovery and crush resistance aspects of scaffolds are described in greater detail in US20110190871.

The term "crush recovery energy" given in units of N*mm refers to the energy or work required to produce the stated amount of crush (as a percentage of the diameter of the scaffold, e.g., 10% crush means the scaffold diameter or height is reduced to 90% of its pre-crush height).

"A simulated walking test" refers to an in-vitro or bench test for axial fatigue of a peripheral scaffold according to the following protocol.

A 6.0 mm inner diameter silicon tubing is axially stretched to 7% of its length and held in this position by attaching its ends to a first (fixed) member and a second, axially movable member of a frame. The second member is a linear actuator. The frame is programmed to axially cycle the silicon tubing back and forth between the stretched state and its original length; this will create a fixed axial percent compression strain to the intended test samples.

The second or first member has an inner lumen in fluid communication with the stretched tubing lumen to allow passage of a scaffold-catheter into the lumen of the stretched tubing. The tube is submerged in a water bath filled with saline at 37 Deg. C such that the testing condition is maintained at relevant environment.

The length of the tubing used for the test depends on the length of the scaffold to be tested. The un-stretched tube has a length about twice the length of the scaffold.

The scaffold is introduced into the lumen of the stretched-tubing via the second end lumen. The scaffold is introduced as a crimped scaffold on a FoxPlus™ 0.035 PTA catheter and advanced into the stretched tubing lumen. The PTA catheter has a 6.0 mm nominal inflation balloon.

The scaffold, when positioned in the tube, is expanded to a post-dilation diameter of 6.5 mm. Balloon pressure is maintained for 2-5 min to minimize recoil and achieve apposition with the walls of the tube.

The second member (coupled to a linear actuator) is programmed to move axially back and forth at a rate of 1 Hz (the length of the stroke is the length to return to the tubing in the un-stretched position) so as to apply an axially-cyclic compressive force.

A "three-month simulated walking test" means 250,000 cycles of 7% compression at 1 Hz using the above test apparatus, wherein the cycles are applied over three consecutive days.

A "six-month simulated walking test" means 500,000 cycles of 7% compression at 1 Hz using the above test apparatus, wherein the cycles are applied over six consecutive days.

$$VRT = A + B + A@B$$

The metrics of functional output leading to VRT may be described generally in terms of the following A and B categories:

A. Mechanical Modulation of the input site or the mechanical behavior of the scaffold after being implanted over time (hereinafter "Input A" to VRT); and B. Cellular conduction and induction—the implanted scaffold's role as a tissue engineering (TE) template (hereinafter "Input B" to VRT).

Figure 23:
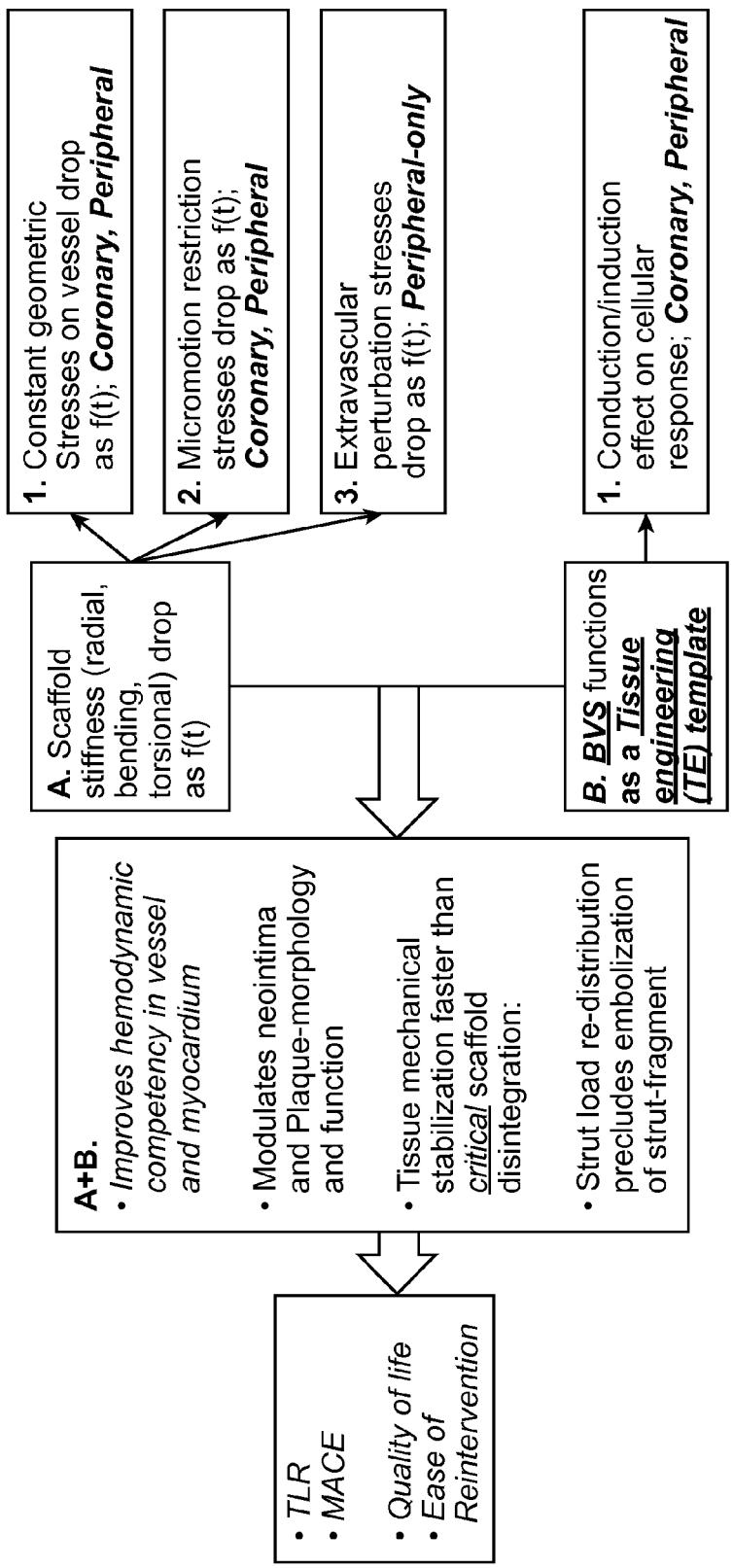
FIG. 23 is a flow diagram summarizing a process of Vascular Restoration Therapy (VRT).

VRT then results from the combined effects, or convolution of A and B. The process is summarized in FIG. 23. These principles can apply to scaffolds made from a a biodegradable, bioabsorbable, bioresorbable, or bioerodable polymer and implanted into a coronary artery or peripheral artery. One of the important distinctions between the coronary and peripheral case, however, is the rate of change in mechanical properties of the peripheral scaffold following implantation changes as necessary for achieving VRT in a peripheral vessel. In both cases, however, the basic principles of VRT are the same, as will be appreciated.

Figure 24A:
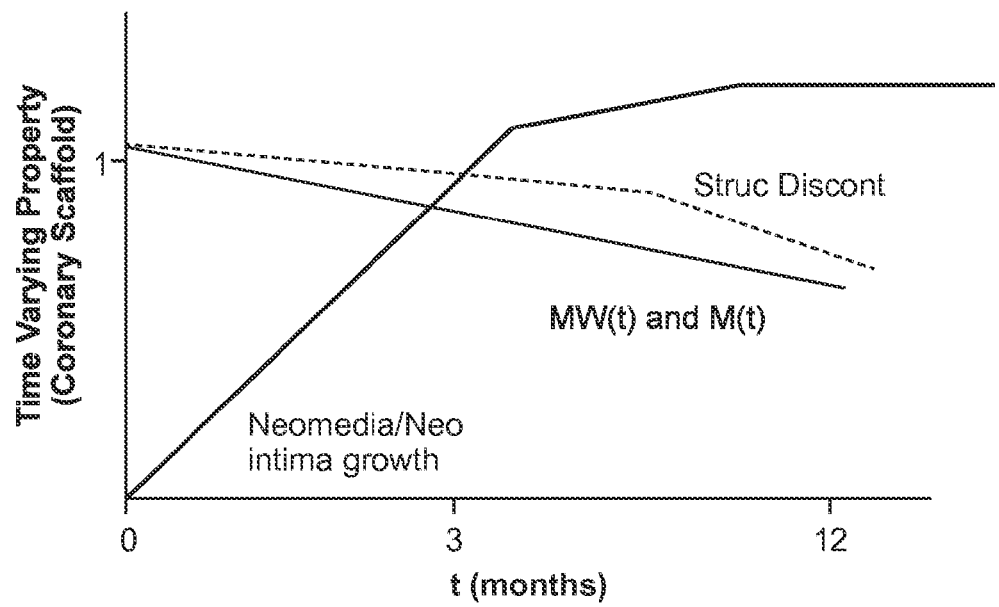
FIGS. 24A and 24B show a comparison between the time-varying mechanical properties of a coronary scaffold and peripheral scaffold.
Figure 24B:
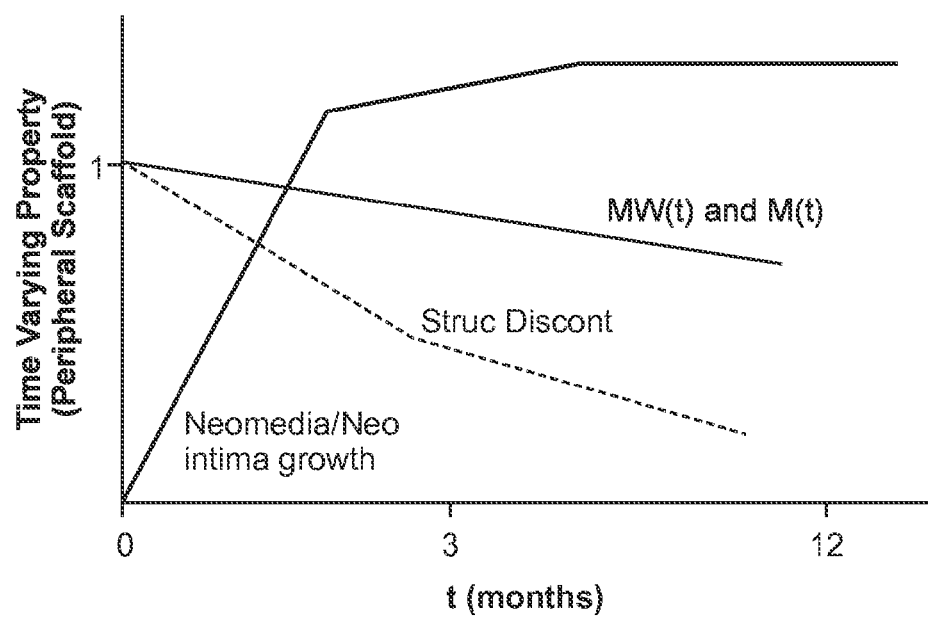

FIGS. 24A and 24B are plots showing, in general, the time-varying properties for a coronary verses a peripheral scaffold according to the disclosure. The plots show time-varying mechanical properties ("Struc Discount"), molecular weight ("MW(t)") and mass ("M(t)") of the scaffolds over a 12 month period following implantation in a coronary artery. FIG. 24B shows the time-varying properties for a peripheral scaffold over a 12 month period following implantation. There is a noticeable change in the scaffold's mechanical properties, e.g., its radial stiffness, as early as one month following implantation for the peripheral case, which may be thought of as a function of the number of developing strut discontinuities or fractures. The coronary scaffold, shown in FIG. 24A, by contrast, begins to breakdown not until much later in time, e.g., 4-6 months after implantation.

VRT-related time constants, for coronary and peripheral scaffolds, are compared below:

| VRT-Time constants | Coronary (mos.) | Peripheral (mos.) |
| --- | --- | --- |
| Vessel scaffolding time | 3 to 4 | 2 to 3 |
| Scaffold threshold integrity retention | Greater than, or 6 | 3 to 4 |
| Scaffold stabilization by Neomedia/Neointimal growth | 5 to 6 | 2 to 3 |
| Critical scaffold integrity loss | Greater than, or 9 | 6 to 9 |
| Time to total mass loss | clinically irrelevant | |

Figure 25A:
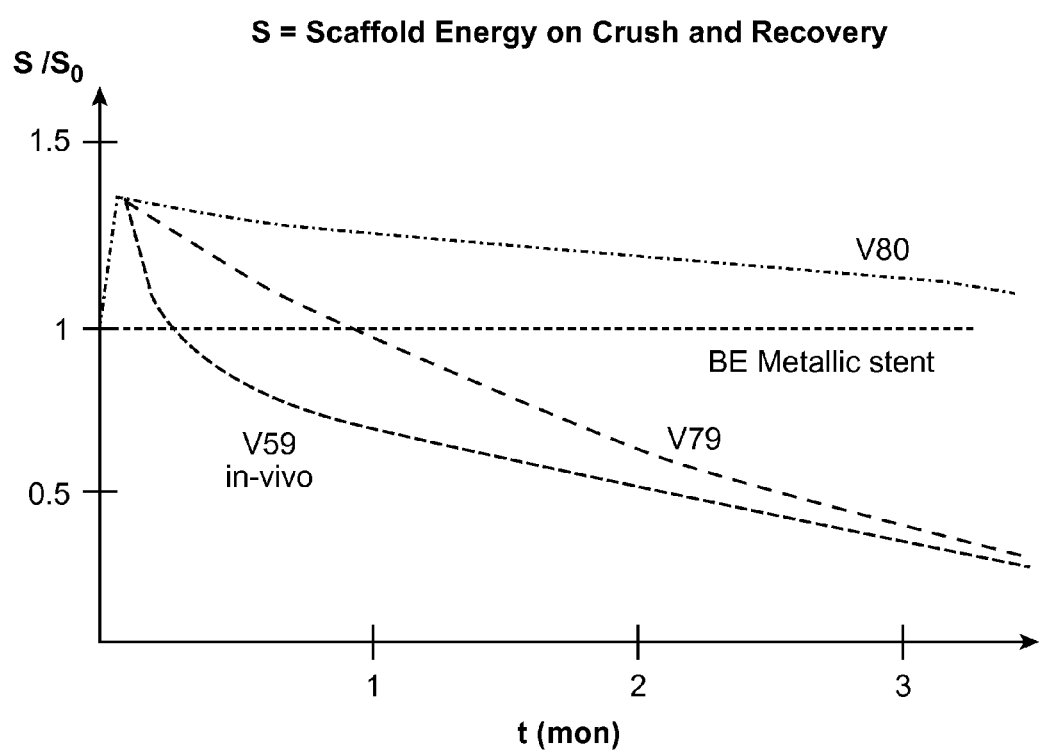
FIG. 25A is a plot showing a change in scaffold crush and recovery for a peripherally implanted V79 and V80 scaffold, as compared to a V59 scaffold.
Figure 25B:
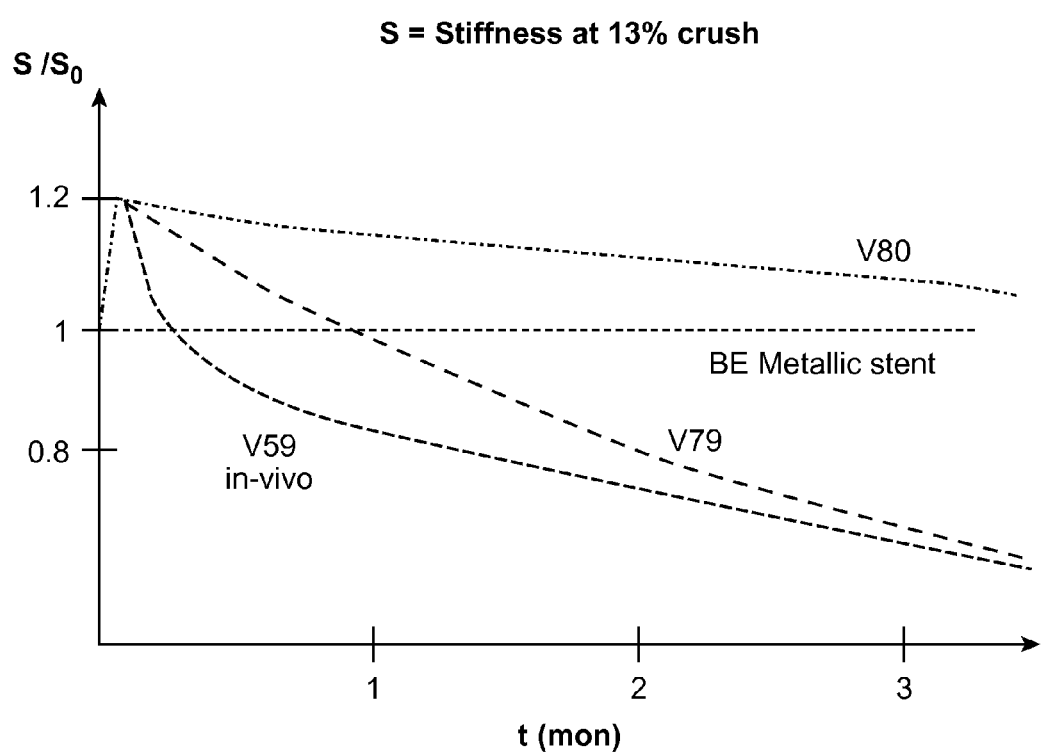
FIG. 25B is a plot showing a change in scaffold stiffness at 13% crush for a peripherally implanted V79 and V80 scaffold, as compared to a V59 scaffold.

Noticeable changes in a coronary scaffold's mechanical properties are mostly attributed to a critical loss in molecular weight of the polymer composition forming the load bearing scaffold structure. The change in the peripheral scaffold mechanical properties is, in contrast, a response to the loading environment in which it is implanted. As FIG. 24B portrays, there is an almost immediate development of strut discontinuities following implantation, e.g., 7% of the scaffold struts fracturing one month from implantation. There is also a more rapid development of a neo-intima layer for the peripheral scaffold than the coronary scaffold. FIGS. 25A and 25B show similar plots for specific embodiments of a peripheral scaffold during the first three months following implantation.

Figure 26A:
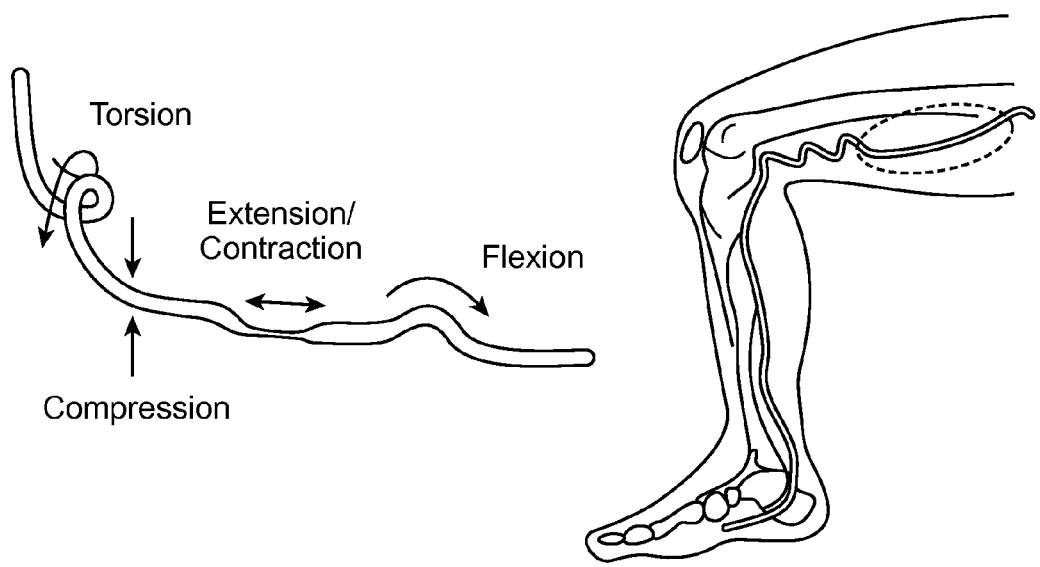
FIGS. 26A and 26B illustrate the dynamics of the femoral artery during normal use of the leg.
Figure 26B:
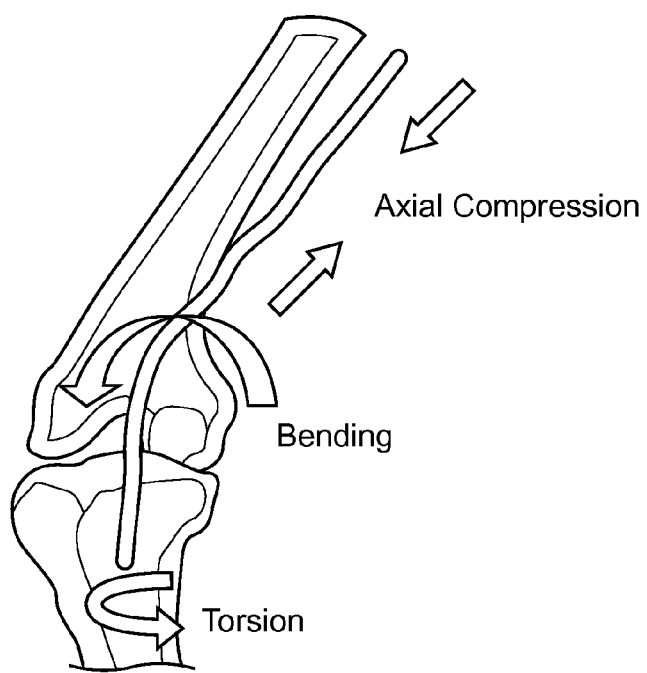
Figure 27:
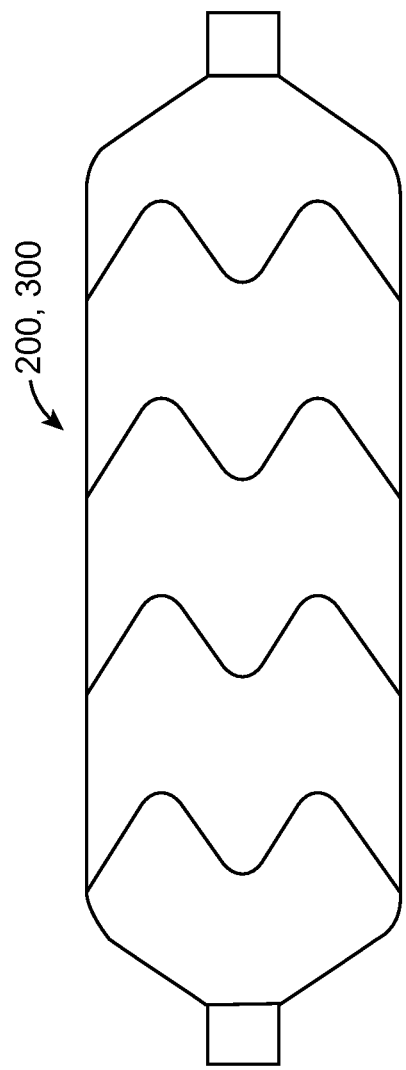
FIG. 27 shows a scaffold 200/300 crimped to a balloon.

The loading on a coronary scaffold is mostly radial, reflecting the periodic contraction and expansion of blood vessels associated with blood flow through the vessels. The peripheral scaffold environment, however, is far more complex. FIGS. 26A and 26B show the types of movement and/or loading of a superficial femoral artery (SFA) of the leg. The vessel undergoes significant torsion, bending, axial contraction and extension and compression (crushing/pinching). For scaffolds implanted within this region, especially when the scaffolds are over about 40 mm in length, it is inevitable that fractures and breakdown of the scaffold begin to occur within the first month, or even within the first 1-2 weeks following implantation. In accordance with the disclosure, this process of breakdown of the scaffold's load bearing structure in a peripheral vessel, e.g., the SFA, however, can be controlled so that the supporting function of the scaffold is provided for only long enough that a neointimal layer has developed and the vessel has been restored to a state where structural support of the scaffold is no longer essential to proper vascular function. Indeed, a controlled reduction in mechanical properties (brought about by the breakdown of the scaffold structure) is believed more beneficial to restoring a more natural vascular function than, e.g., a scaffold or stent that retains its mechanical supporting properties beyond that needed to support the vessel. After the vessel has begun to repair itself, a scaffold that remains relatively radially and/or axial stiff is believed an impediment to the healing process. Thus, in accordance with the disclosure the controlled development of strut discontinuities in a scaffold is believed a necessary condition for Input A to VRT.

The design and mechanical properties of a peripheral scaffold supporting the VRT objective, i.e., Input A to VRT, will now be discussed in greater detail. This general discussion is then followed specific examples of time-varying attributes of preferred scaffold designs.

Input A to VRT: Mechanical Modulation of the Implant Site as a Function of Time.

1) Bioresorbable Design Metric:

i. The "M" Parameter

The "M parameter" refers generally to the scaffold's geometry and behavior resulting from that geometry. That is, the number of crowns, linking elements, number of crowns, the angles between crowns, the wall thickness, etc. Thus, an "M" parameter refers to such things as the height, width, thickness of struts and crowns, number of crowns, number of rings, outer diameter, and wall thickness. This category therefore defines the idealized flexural rigidity of struts, hoop strength/stiffness, radial strength (as defined in WO2011094621), radial stiffness, and related structural mechanics for the scaffold given the material used and dimensions of the load-bearing and interconnected elements.

Tables 1-2 and FIG. 6A provide examples of some or all of the features from which an M parameter, which is a number, may be based.

ii. Polymer Selection and Degradation Profile.

This aspect of the design input refers to the choice of material, and its sequence of polymer-molecular weight, strength and mass reduction over time, see e.g., Middleton John C, et al *Synthetic biodegradable polymers as orthopedic devices* (Biomaterials 21 (2000) 2335-2346)(FIG. 10), for the particular polymer or polymer blend used to form the backbone or scaffold of the load-bearing bioresorbable structure. As noted above, for a coronary scaffold the point in time when there is critical loss in molecular weight signals the time when there is a reduction in mechanical properties of the scaffold, e.g., radial stiffness. This phenomenon typically begins to occur within 4-6 months following implantation. For a peripheral scaffold according to the disclosure the loading environment and design produces a reduction in mechanical properties far sooner. As such, according to embodiments disclosed the peripheral scaffold loses most of its radial support capability well before the 4-6 months period followed implantation.

iii. Scaffold Processing History; Temperature and Force Profile Over Time, Exposure to Moisture, Gas, and Energy.

This aspect of design refers to the processes used to arrive at an implantable medical device. Unlike a metal stent, the processing conditions for forming a polymer tube from which a scaffold is made can greatly affects properties such as its lowest crimping profile, deployment profile, and radial strength/stiffness. In a preferred embodiment the scaffolding is formed from a tube cut to form the scaffold's network of interconnected struts and linking elements. A process for forming the tube is described in U.S. patent application Ser. No. 12/558,105. The processing parameters include extrusion then biaxial expansion of a tube within a prescribed temperature range to increase the radial strength of the tube while maintaining a desired amount fracture toughness in the expanded tube. After forming the scaffold, it is then crimped to a balloon. The crimped scaffold is then sterilized, either by a gas or by E-beam radiation. The scaffold is plastically deformed from its crimped state when implanted within a vessel. Additional effects of the processing condition include the pre-crimp, crimped and deployment diameters (all of which can be different from each other), and recoil of the scaffold after being implanted within the vessel.

2) Functional Output Metric

1. Flexible Navigation Through the Vessel and Easy Deployment.

The crossing profile of the crimped scaffold and manner in which the scaffold was crimped influences this functional output. It has been found that a bioresorbable, balloon-expanded PLLA scaffold is particularly sensitive to the crimping process. The crimping process can affect not only the structural integrity of the crimped scaffold, but also its ability to deploy uniformly. If deployed non-uniformly or with significant crack propagation (as a result of the crimping process) then several stress concentrations can develop, which can cause premature failure or strut discontinuities.

The ability to flexibly navigate through a vessel also requires a sufficient retention force on the scaffold, to prevent it from becoming dislodged. However, for a peripherally-implanted scaffold this is sometimes not an issue since the scaffold is significantly longer than a coronary scaffold.

2. Radial/Pinch Strength and Stiffness at t=0
I. Pre-Implant (Scaffold-Only)
II. Immediate Post-Implant (Implanted Segment In Vivo)

As discussed in greater detail, below, the pre-implant stiffness can vary greatly from the as-fabricated, or as crimped stiffness. The effects on the scaffold's stiffness at the time of implantation can be reduced significantly due to such combined effects as sterilization and shelve life, either of which can cause the radial stiffness/strength to decrease and/or its brittleness in increase. Immediately following implantation, however, the stiffness/strength can increase dramatically, e.g., double, as a result of hydration within the vessel.

3. Rate of Decrease in Radial Strength, Radial and Stiffness, Pinch Strength, Pinch Stiffness, or Crush Energy as a Function of Time In Vivo.

It is desirable to design a bioresorbable scaffold with a controlled initial increase followed by a gradual decrease in scaffolding property such as radial strength, radial stiffness, pinch strength, pinch stiffness, or crush energy as a function of time and its integration into the vessel wall. The functional form of this stiffness variation over time, i.e., f(t), is described in greater detail below. The initial increase in strength/stiffness allows the design of the implant to be less rigid and low modulus pre-implant, while successfully creating patency within occlusive strictures by scaffolding at higher radial strength/stiffness for the initial time period, i.e., within the first 10 days following implant.

As discussed in greater detail below, optimal strength and stiffness, and optimal rate of decrease in strength and stiffness reflects a balance between strength and ductility or resistance to excessive discontinuities, while at the same time achieving a gradual decrease in strength/stiffness/crush energy over time (by way of discontinuities or fractures in the scaffold structure, including struts forming rings and linking elements). In one particular preferred embodiment, e.g., V80, the stiffness and strength at t=0 is significantly lower than prior designs for purposes achieving the optimal rate of change in stiffness over the period of about 0-3 months. Examples of scaffold structural characteristics having a direct influence on the M parameter for V80 at t=0 are provided in FIGS. 4, 5A and 6A, and TABLE 2 and 4.

3) Design and Function in Relation to VRT Goals

The design and functional metrics of the scaffold then provide the following favorable qualities for VRT: (1) decrease in average forces to the vessel (e.g. vessel geometry re-structuring, outward radial force); and (2) decrease in resistance to Fluctuation forces derived from vessel tonicity and pulsatility (e.g., compliance mismatch with native vessel).

As the scaffold's radial stiffness (primarily) decreases over time (as a result of fracturing struts) its force influence on the healing vessel tissue concomitantly decreases. This re-balancing over forces between vessel and scaffold is believed favorable and better promotes healing than the case where the scaffold radial stiffness more or less stays the same over this time period, such as in the case of non-bioresorbable metal stent (FIG. 24).

The change in mechanical properties resulting from the fracturing structure also provides the additional benefit of causing the combined structural dynamics of the vessel and implanted scaffold to converge towards that of the native vessel (as the vessel heals). Thus, as the scaffold becomes more compliant, or as the inter-ring forces of the scaffold become more and more de-coupled from each other, the vessel is permitted to return to a harmonic motion (as blood rushes through the vessel) so that it becomes more like that of neighboring native vessel segments. The scaffold's ability to drive or influence the natural harmonic motion of the vessel gradually decreases as the structural integrity of the vessel improves.

4) Analytic Modeling of Decrease in Stiffness Over Time (Exponential Decay) as a Design Input Parameter The approach taken to model and design the scaffold to achieve the foregoing benefits may begin with defining time constants defining the initial rise in stiffness/strength following implantation and the decay period, from the time of greatest strength/stiffness to the value for strength and stiffness that the scaffold will eventually after a predetermined period, e.g., 3 months. A first criterion is a safety-related criterion, which requires that the time period from implantation until critical scaffold integrity loss, e.g., ½ of radial strength or stiffness loss is greater than the time period needed to achieve tissue stability. Or, in terms of a time constants, $$K_B > K_A$$

Where $K_B$ is the rate constant of neointimal formation and $K_A$ is the rate constant for critical scaffold disintegration. The criterion is enforced on the design for the purpose of minimizing chances that an embolization could occur within a vessel due to excessive strut discontinuities occurring before a neointimal layer has sufficiently developed over the scaffold body. Thus, the design (M parameter, etc.) needs to take into consideration avoidance of host-material interaction resulting in adverse safety events occurring during the absorption process.

EQ. D1 is used to represent the characteristics of the scaffold's time rate of change in stiffness/strength (as a ratio of a starting value) as an indicator of the scaffolded vessel's response to an applied load.

$$S(t)/S_O = S_{OV}/S_O + (1 - S_{OV}/S_O - C)e^{-t/k} + Ce^{-t/K_o}, \quad \text{(EQ. D1)}$$

where $S(t)/Sov = (S(t)/So)*(So/Sov)$
$S(t=0)/So=1$

Examples of plots of EQ. D1 for specific scaffold designs are reproduced as FIGS. 25A-25B. TABLES 1.1-1.5 and the accompanying discussion below further disclose a method for representing the time-varying pinching stiffness for scaffolds, utilizing explant pinching stiffness data, in terms of EQ. D1. This relationship of the coefficients to physical quantities and their constitutive relationships to other equations follow.

So can be the radial strength, radial stiffness, crush strength or crush stiffness of scaffold at t=0; So=g(Xi design, Xi mat, Xi process); So=g(M) for a given process and materials Variable set (Xi design) depends on M parameter. As mentioned earlier, So also depends on crimping process, time lapse after sterilization, sterilization and other processes, in addition to the M parameter.

Sov is the radial strength/stiffness or crush strength/stiffness of the reference vessel;

S(t) is the radial strength/stiffness or crush strength/stiffness of the scaffold, e.g. t=0 . . . 3 months;

K=f(Xi design, Xi mat, Xi process); K=f(M) for a given process and materials; where "M" refers to the "M parameter" reflecting the decrease in scaffold properties as struts fracture; and C, Ko=g(Xi design, Xi mat, Xi process); KO, C=g(Mo) where Mo refers to an M parameter reflecting the initial rise properties of the scaffold after implantation.

The "Xi" (design, material and process for making the scaffold) refer to the variables (discussed earlier) in design affecting the value of K, Ko, C. "K" is the time constant for occurrence of strut discontent, a longer time phenomena; "C" and "Ko" describes the intensity and time constant respectively for the stiffness/strength rise, a shorter time phenomena. Therefore Ko<<K in EQ. D1. Value of C determines how much initial stiffness occurs. Ko and C characterize the initial stiffness/strength rises upon implantation due to wetting, plasticization, and polymer chain orientation. This is a short time-constant phenomena starting from right after implant and completing by 2-3 days, one week or two weeks. Therefore Ko is always much smaller than K.

EQ. D1 was derived from the hypothesis that the time rate of range of the difference between a scaffold's stiffness S(t) and native or diseased vessel stiffness Sov, d(S–Sov)/dt can be approximated as follows:

$$d(S-Sov)/dt = R*f(t) - M*(S-Sov)^n \quad \text{EQ. D2}$$

Where f(t) is a general function of time. Based on observed explants of scaffold the exponential form was believed to be a good choice for f(t) and n=1 a good approximation for the power. R is a factor accounting for the observed increase in radial strength and stiffness of the scaffold that had occurred during the first two-weeks following implantation. This increase in stiffness is due to hydration of the polymer material, as discussed above. The same effects have been seen in bench tests. Page 3 of APPENDIX I (U.S. Provisional Application Ser. No. 61/717,613) shows scaffold work done (N*mm) on explants from animal data for the V59 scaffold for shortly after implantation, and one week and two weeks after implantation. The "V59 control" shows the value for a scaffold prior to implantation. As can been seen in these plots, there is a significant rise. This is the R term. Pages 1, 2, and 4-6 show similar results for stiffness for bench testing for the V80 (described in detail below) and the V59.

Page 1 of APPENDIX I shows an increase in both radial strength and K-Lnorm after 3 days submerged in water at 37° C. and after undergoing 250 k cycles of axial loading of between 7% axial compression of the scaffold (as a percentage of the scaffold total length). There were about 10% observed strut fractures from scaffolds that had gone through 250,000 cycles of axial fatigue testing (3-month simulated walking).

Page 3 of APPENDIX I (ex-vivo flat plate testing data done w/V59 scaffolds implanted w/in vessels) indicates a minimal difference between V59 0 d (scaffolds inside arteries) vs. V59 Control (scaffolds only, no artery present). After 7 days post implant, an increasing of >35% in crush recovery energy (N*mm) was observed when compared to V59 0 d (13.5 N*mm vs. 10.0 N*mm).

Pages 4-5 of APPENDIX I show an increasing of up to about 100% in radial strength of 3-month aged V79 and V80 devices (crimped onto 2 different balloon catheters 0.018" vs. 0.035") post 6 days of hydration from 500,000 cycles of axial fatigue (six-month simulated walking test). These graphs show the variation in increased strength/stiffness depending on the amount of crimping that was done from an initial crimp size).

Referring again to EQ. D2 the "M" is the M parameter discussed earlier. It is a constant value determined from the design, materials, fabrication process, etc. as discussed above. Thus, there is some unique value, called the M parameter for the scaffolds V79, V80, etc. that is used solely for convenience, so that d(S–Sov)/dt may be expressed in a convenient and more intuitive form reflecting observations during test.

Similarly, the scaffold stiffness prior to implantation, or So and the time constants K, Ko may be expressed in terms of an M parameter, or Mo parameter (where Mo reflects the properties of the scaffold that gives it the initial rise within the about two weeks following implantation (and prior to the onset of fractures) as opposed to later-stage stiffness/strength properties represented by M). Again the concept of "M parameter" of "Mo parameter" is a value unique to every scaffold and based on its design, material, etc. From this representation of the problem the "C" in the equation above is equal to R/So (M–Mo), where C is a factor associated with the initial rise in strength/stiffness.

Coefficient values and ranges for embodiments of EQ. D1 have been estimated for the V59, V79, and V80 scaffolds. These coefficient values are given in TABLE 1A, along with ranges of these coefficients for other embodiments of a peripheral scaffold according to the disclosure. Utilizing EQ. D1 and these coefficients time varying peripheral scaffold properties may be estimated, preferably over the first 6 months following implantation, more preferably 3 months following implantation, and more preferably within the first month, or on or about 7, 28, 60, 90 and/or 180 days after implantation.

With reference to TABLES 1.1-1.5, below, the following describes a process for estimating a rate of change of a mechanical property over a period of 7 to 90 days following implantation. The objective is twofold.

First, one wants to utilize extensive explant data over the 7 to 90 day time period (in the example below, the V59 scaffold) to estimate changes in mechanical properties for similar scaffolds (in the example below, the V79 and V80 scaffolds). The scaffolds are said to be similar based on an understanding of mechanical properties and testing (in-vitro) to enable one to reasonably account for differences (see FIGS. 7-22 showing testing).

Second, one wants to arrive at ranges for the coefficients in EQ. D1 based on the knowledge gained from the differences between key coefficients affecting the first and second exponential decay terms in EQ. D1 based differences between the scaffolds, e.g., differences between the V59, V79 and V80, in combination with the differences in the scaffold properties. From this comparison, a design tool can be used for Input A to VRT that provides the time-varying metric to a scaffold design process.

Estimates for time-varying pinching stiffness properties for the V79 and V80 scaffold, based on in-vitro data and limited in-vivo data (7 and 28 days) for these scaffold, and more extensive in vivo today for V59 (7 to 90 days) may be determined in the following manner.

In the following example, percentile fracture is known for V59, V79 and V80 for 0, 7 and 28 days after implantation in an animal model. Also, a ratio of pinching stiffness S/SO for V59 explants from the animal model is known for 0, 7 and 28 days (as well 14, 28, 90, 180 and 265 days, see TABLE 1.1). S/SO is only known for 0 and 7 days for V79 and V80. However, based on in-vitro tests of V79, V80 it is believed that for time intervals of 1, 2, and in some cases 3 months from implantation the percentage fracture in combination with the in-vitro data (e.g., simulated walking test) and material properties (e.g., stiffness, strength, toughness, etc.) can be utilized to provide reasonably accurate estimates of S/SO, e.g., ratio of pinching stiffness for an explant, to the extent that a working model of time-varying mechanical properties can be formulated to assess a scaffold's fitness for use prior to in-vivo validation.

The first step is to calculate a slope for ln(SO/S) verses ln(1−d) for the V59, where ln(SO/S) is the natural log of the pre-implant pinch stiffness over the post-implant pinch stiffness for the V59 and ln(1−d) is the natural log of the number of intact struts found in the V59 explant (d=is the number of discontinuous struts, as a percentage of the total). It can be shown that this slope is 1.24 for the V59. Using this slope, EQ. B1 is used to estimate S/SO for later time points (as a function of the percentage of discontinuous struts).

$$S/SO = S7/S0 * ((1-d)/(1-d7))^{1.24} \quad \text{(EQ. B1)}$$

The data in TABLE 1.1 indicates that the EQ. B1 provides good estimates (col. 6) of the actual S/SO values (col. 3) for the V59. Based on this conclusion, EQ. B1 is then used to estimate S/SO for V79 and V80 at 7 and 28 days from implant. These estimates are provided in col. 5 of TABLE 1.2.

TABLE 1.1

| time, days | % discount. struts | stiffness ratio (S/SO) | Ln s/s0 | Ln (1 − d) | Validation of measured values using EQ. B.1 |
|---|---|---|---|---|---|
| 0 | 0 | 1.00 | 0 | 0 | |
| 7 | 7.28 | 1.15 | −0.14 | 0.08 | 1.15 |
| 14 | 20.60 | .931 | 0.07 | 0.23 | 0.95 |
| 28 | 39.20 | .742 | 0.30 | 0.50 | 0.68 |
| 90 | 54.00 | .481 | 0.73 | 0.78 | 0.48 |
| 180 | 57.00 | .197 | 1.62 | 0.84 | 0.44 |
| 365 | 76.00 | .065 | 2.74 | 1.43 | 0.21 |

TABLE 1.2

| | % discont. struts at 28 days from explants | % discont. struts at 7 days from explants | S7/S0 (7 day pinch stiffness ratio) | EQ. B1 estimates of S/SO at 28 days |
|---|---|---|---|---|
| V59 | 40 | 7.28 | 1.15 | 0.68 |
| V79 | 13 | 0.00 | 1.30** | 1.09 |
| V80 | 7 | 0.00 | 1.30** | 1.19 |

**1.3 for S/SO at 7 days is derived from the in-vitro data, which is believed a good estimate given no discontinuous struts found in V79, V80 explants after 7 days.

Next, coefficients for EQ. D1 are estimated for the V59, V79 and V80 scaffolds, as well as a range for a SCAFFOLD 1 type and SCAFFOLD 2 type. The coefficients are shown in TABLE 1.3.

The coefficients for time-varying properties governed by EQ. D1 for embodiment SCAFFOLD1 and SCAFFOLD2 are based on the differences in the M parameters, e.g., struts, crowns, links, between V59, V79 and V80, the longer term V59 explant data, simulated walking tests and measured static properties from the in-vitro tests for V2, V23, V59, V79, V80, V62, and V78. SCAFFOLD1 has a backbone structure similar to V80, but with M parameter variations (e.g., ratio of diameter to wall thickness, strut width to thickness ratio, crown angles and radius and/or processing parameters such as biaxial expansion in radial and axial direction taken into consideration). SCAFFOLD2 is similar to the range of scaffolds studied in TABLE 3, but with M parameter variations taken into consideration for these scaffolds. See TABLES 3-4 below, FIGS. 7-22, APPENDIX I and accompanying discussion below.

TABLE 1.3

| Coeff. (EQ. D1) | Units | V59-ex vivo | V80-ex vivo est. | V79-ex vivo est. | SCAFFOLD1 | SCAFFOLD2 |
|---|---|---|---|---|---|---|
| R/S0 | (1/day) | 0.40 | 0.51 | 0.57 | 0.45-0.6 | 0.45-2.5 |
| Ko | day | 0.65 | 0.65 | 0.65 | 0.66-2.0 | 0.66-7.0 |
| K | day | 60.00 | 250.00 | 125.00 | 200-375 | 70-1000 |
| c | ratio | −0.26 | −0.33 | −0.37 | (−0.3) to (−1.2) | (−0.275) to (−2.5) |
| $S0/S0_{V59}$ | S0 ratio, with respect to V-59 | 1.00 | 0.50 | 1.00 | 0.35-0.75 | 0.25-0.95; or 1.1-2.0 |

Embodiments contemplated include scaffolds having time-varying mechanical properties satisfying EQ.D1 over ranges of 1 month, 2, months, and 3 months from implantation.

The coefficients generated above, when used with EQ. D1 produce the estimates of in-vivo pinch stiffness ratios provided below as TABLE 1.4. The columns 2-4 show the predicted S/SO for each scaffold using EQ.D1 and column 5 provides the measured S/SO from the V59 explant data.

TABLE 1.4 values for S/SO for V59, V79, V80 using EQ. D1 and compared to V59 explant data (S = pinching stiffness at time t; S0 = pinching stiffness at time of implant)

| days | V79 S/S0 | V59 S/S0 | V80 S/S0 | V59 explant |
|---|---|---|---|---|
| 0 | 1.00 | 1.00 | 1.00 | |
| 3 | 1.34 | 1.20 | 1.31 | |
| 7 | 1.30 | 1.12 | 1.30 | 1.15 |
| 12 | 1.25 | 1.04 | 1.27 | |
| 14 | 1.23 | 1.00 | 1.26 | 0.93 |
| 21 | 1.16 | 0.89 | 1.23 | |
| 28 | 1.10 | 0.80 | 1.19 | 0.74 |
| 35 | 1.04 | 0.71 | 1.16 | |
| 42 | 0.98 | 0.63 | 1.13 | |
| 52 | 0.91 | 0.54 | 1.09 | |
| 60 | 0.85 | 0.47 | 1.05 | |
| 75 | 0.76 | 0.37 | 0.99 | |
| 90 | 0.67 | 0.29 | 0.94 | 0.48 |
| 105 | 0.60 | 0.23 | 0.88 | |
| 120 | 0.53 | 0.18 | 0.83 | |
| 150 | 0.42 | 0.11 | 0.74 | |
| 180 | 0.33 | 0.07 | 0.66 | 0.20 |
| 210 | 0.26 | 0.05 | 0.59 | |
| 240 | 0.21 | 0.03 | 0.52 | |
| 270 | 0.17 | 0.02 | 0.47 | |
| 310 | 0.12 | 0.02 | 0.40 | |
| 360 | 0.09 | 0.01 | 0.33 | 0.06 |

The values for So depend on the time spent between initial fabrication and assembly of the scaffold and catheter and when it is implanted. S(t) above represents the ranges of increase in radial stiffness expected for the scaffold, corresponding to the time constant Ko.

After implantation tests and in-vivo data show that scaffold properties such as stiffness can increase to about 1.3 or more times a pre-implant value, as shown, e.g., in TABLE 1.4 and other tests. After this period of time, developing fractures cause the stiffness to decrease. This is represented in the examples of FIGS. 25A-25B and TABLE 1.4 above as well.

This initial rise in both radial and crush strength/stiffness is expressed by the second exponential term $Ce^{-t/Ko}$ in EQ. D1. It is a function Ko (time constant for the initial rise). Since the initial rise occurs only over a relatively short time, Ko<<K.

A decay in both crush and radial strength/stiffness, which is attributed to fractures developing in the scaffold, is represented by the second exponential term $(1-S_{OV}/S_O-C)$ $e^{-t/k}$ in EQ. D1. As can be seen in the curves, EQ. D1 fits well to the V59 in vivo data.

Slope for $S(t)/S_o$ $$d(S(t)/S_o)/dt = -1/k(1-S_{OV}/S_O-C)e^{-t/k}-C/Ko\ e^{-t/Ko} \quad \text{(EQ. D3)}$$

Curvature for $S/S_o$ $$d^2(S(t)/S_o)/dt^2 = 1/k^2(1-S_{OV}/S_O-C)e^{-t/k}+C/Ko^2 e^{-t/Ko} \quad \text{(EQ. D4)}$$

The slope is negative, but the curvature is positive, which is what is seen in the in vivo data. After an initial increase in fracture and concomitant loss in radial strength/stiffness the strength and/or stiffness begin to converge to a constant value. Moreover, this convergence occurs well before there begins a significant loss in molecular weight of the bioresorbable polymer. This phenomenon may be understood from the following. After a certain number of struts/links have fracture, the remaining intact structure has less forces applied to it. The structure becomes much weaker, but settles to stiffness and strength values sufficient for purposes of VRT. The vessel after a certain time period has healed and does not need the scaffolding for supporting the walls. The scaffold has done its purpose and is not needed any longer as the primary load-bearing member.

TABLE 1.5 shows slopes for V59, V79 and V80 using EQ.D3. The values in TABLE 1.5 are the computed slopes multiplied by a factor 100. Thus, for example, the slope or rate of change in S/SO at day 7 for the V80 is $-0.51 \times 10^{-2}$/days. As indicated, there is an initial sharp rise in the slope, followed by a gradual decrease.

TABLE 1.5

Values for EQ. D3 for V59, V79 and V80 (100 * d(S(t)/S_o)/dt)

| t, days | V79 | V59 | V80 |
|---|---|---|---|
| 0 | 56.21 | 38.35 | 50.61 |
| 3 | −0.50 | −1.59 | −0.01 |
| 7 | −1.03 | −1.86 | −0.51 |
| 12 | −0.99 | −1.71 | −0.50 |
| 14 | −0.97 | −1.65 | −0.50 |
| 21 | −0.92 | −1.47 | −0.48 |
| 28 | −0.87 | −1.31 | −0.47 |
| 35 | −0.82 | −1.17 | −0.46 |
| 42 | −0.78 | −1.04 | −0.44 |
| 52 | −0.72 | −0.88 | −0.43 |
| 60 | −0.67 | −0.77 | −0.41 |
| 75 | −0.60 | −0.60 | −0.39 |
| 90 | −0.53 | −0.47 | −0.37 |
| 105 | −0.47 | −0.36 | −0.34 |
| 120 | −0.42 | −0.28 | −0.32 |
| 150 | −0.33 | −0.17 | −0.29 |
| 180 | −0.26 | −0.10 | −0.26 |
| 210 | −0.20 | −0.06 | −0.23 |
| 240 | −0.16 | −0.04 | −0.20 |
| 270 | −0.13 | −0.02 | −0.18 |
| 310 | −0.09 | −0.01 | −0.15 |
| 360 | −0.06 | −0.01 | −0.12 |
| 450 | −0.03 | 0.00 | −0.09 |

TABLE 1.5-continued

Values for EQ. D3 for V59, V79 and V80 (100 * d(S(t)/S_o)/dt)

| t, days | V79 | V59 | V80 |
|---|---|---|---|
| 540 | −0.01 | 0.00 | −0.06 |
| 730 | 0.00 | 0.00 | −0.03 |

Based on the foregoing, in some embodiments, a slope or rate of change in a mechanical property (×100) with respect to time over the interval of greater than about 7 days and up to 3 months from implantation may range from about −1 to −0.37, more narrowly, about −0.5 to −0.3, and about −0.8 to −0.2. In some embodiments, the slope may be, for between 7-28 days between about −0.55 and −0.45, and −1 to −0.8. The slope may be, in some embodiments, for between 28 and 60 days between about −0.45 and −0.35, or −0.55 to −0.35. It is understood that these slope ranges at both endpoints are divided by 100. Moreover, all of the above slope value ranges may be present in a scaffold structure made from a polymer composition comprising PLLA, have rings connected by link elements and a ring may have 8 to 12 crests, 8 crests, 12 crests, and at most 2 links, or at most 3 links. All of the foregoing slopes, of the range of 1-3 months, 1 month, 2 months, or a slope over a day (as provided above) are within the scope of the invention.

FIGS. 1 through 6B and the discussion below describe the M parameter elements pertaining to the scaffolds in TABLE 2.

TABLE 2

Input A to VRT parameters (pre-implant)

| | V59 | V76 | V79 | V80 |
|---|---|---|---|---|
| Outer diameter (mm) | 8 mm | 7 mm | 7 mm | 7 mm |
| Wall thickness (in) | .011 in | .011 in | .011 in | .011 in |
| Crush recovery | See TABLE 3B | See TABLE 3B | See TABLE 3B | See TABLE 3B |
| K-norm (N/mm) (FIG. 22) | 8*(1.24) = 9.92 | 7*(1.64) = 11.48 | 7*(1.46) = 10.22 | 7*(1.09) = 7.62 |
| Radial Strength (N/mm) | .65 | .93 | .78 | .55 |
| In-vivo percent strut fractures (28 days) | 28-38 | 11 | 13 | 8 |
| Number of crowns per ring | 8 | 8 | 8 | 12 |
| Number of links connecting rings | 4 | 3 | 3 | 2 |
| Scaffold material | PLLA | PLLA | PLLA | PLLA |
| Scaffold fabrication process | Biaxial expansion of PLLA extruded tube (processing conditions and resulting morphology as described U.S. application Ser. No. 13/840,257 filed Mar. 15, 2013 (Attorney Docket 104584.47) which is cut into scaffold pattern using laser parameters as described in Table 2 of US20120073733. | | | |
| Scaffold - catheter assembly | Crimp scaffold to 2.03 mm outer diameter using the process described on FIG. 3A of U.S. application Ser. No. 13/644,347 (62571.675). Scaffolds crimped to 6.0 mm balloon. Scaffold-catheter assemblies are then sterilized using E-beam radiation. | | | |
| Scaffold deployment | Scaffolds deployed to about 6.5 mm outer diameter within an about 6.0 reference vessel diameter (in-vivo) or 6.4 tube (in-vitro). | | | |

The time interval most critical to a peripheral scaffold's ability to provide a structural property to the vessel, for purposes of VRT, is the first three months following implantation. It is preferred to have a gradual drop in a mechanical property of the scaffold following implantation, such that after 28 days the scaffold has retained about the same mechanical properties it had proper to implantation.

B. Cellular Conduction and Induction Phenomena Responding to a Tissue Engineering (TE) Template.

Input Type B to VRT is now discussed. The Type B input to VRT refers to B=Cellular conduction and induction phenomena responding to a Tissue engineering (TE) template. The bioabsorbable scaffold acts as a TE template. Metrics for the Type B input to VRT include:

High scaffold surface to volume (S/V) ratio varies with increased strut discontinuity provides a TE template. Therefore, the S/V ratio is a f(t).

Evolution of texture during degradation provides a TE template. Thus, a roughness of the scaffold surfaces is a f(t).

Degradation product of PLLA scaffold—Lactic acid and PLA low MW entity. These by-products of the degradation product have an inductive effect on tissue ingrowth and healing. Therefore, the distribution of MW(t) and Lactic acid is a f(t).

(the phrase "as/is a f(t)" throughout the disclosure means "as/is a function of time"). Specific embodiments include a V62, V79, V76, V78 or V80 scaffold having a 7 mm as-cut or as-fabricated outer tube diameter, wall thickness of 0.011 in, between 8-12 crests, 2 link elements between rings, and a length of 35 to 38 mm.

A metric of Vascular Restorative Therapy is cellular conduction and induction phenomena responding to the bioabsorbable scaffold which acts as a Tissue engineering (TE) template. In general, tissue engineering is the science of persuading living systems to regenerate or repair tissues that fail to heal spontaneously. In one approach, a template that supports and guides the generation of new tissue is implanted into a living system to facilitate tissue repair. Tissue engineering templates use a combination of engineering design and material selection to create performance-driven components that guide the generation of new tissue.

In the case of a bioabsorbable vascular scaffold, endothelial and smooth muscle cells grow over the scaffold body after implantation. This process is usually referred to as endothelialization. Endothelialization is an important part of the healing process with a bioabsorbable scaffold. Endothelialization refers to coverage of a surface with endothelial tissue or endothelial cells. Through this process, the scaffold can become embedded within an endothelial layer and smooth muscle cells. At later stages, significant mass loss occurs resulting in complete absorption of the scaffold.

An implanted bioabsorbable scaffold has a time dependent behavior and biological response. This is described in detail in US2011/0066223, US2011/0066225 and US2010/0198331, which show a decrease in radial strength beginning at about three months after a scaffold is implanted. The scaffold depicted is assumed to not develop any significant fracturing that would affect the radial strength, or otherwise have a change to its radial strength until about three months after implantation. This is the case for certain types of implanted bioresorbable scaffolds, such as coronary scaffolds. For a peripherally implanted scaffold, however, the radial strength does change significantly and well before the three month period has passed, due to the onset of significant fracturing in ring struts relatively earlier into the patency period. The preceding analysis utilizing EQ. D1 and the explant data demonstrate this breakdown process.

Generally speaking, upon implantation the molecular weight of the polymer of the scaffold decreases due to chemical degradation which eventually leads to a decrease in strength of the polymer. The decrease in polymer strength contributes to a decrease in radial strength of the scaffold. Scaffold integrity loss also occurs in the form of strut discontinuities, or fractures. Strut discontinuities may occur at the links in the scaffold resulting in partial or complete decoupling of the rings of the scaffold. Such link discontinuities can result in little or no loss in radial strength.

Therefore, without being limited by theory, the decrease in radial strength for an implanted peripheral bioabsorbable polymer scaffold can be due to two contributions: (1) decrease in the polymer strength arising from molecular weight decrease from degradation (2) fracture or discontinuities in the scaffold struts. Contribution (1) tends to cause a rather abrupt drop in radial strength, although timing of that change depends heavily on the polymer molecular structure and morphology (e.g., around 3 months post-implantation—see FIG. 5B of Exhibit G). The data disclosed herein suggest that contribution (2) tends to cause a gradual decrease in the radial strength with time starting within a few weeks post-implantation. It is believed that the rate of fracturing initially increases then decreases until no further fracturing occurs, since the radial strength appears to approach or reach a steady state value. It is further believed that a scaffold can be designed such that the contributions that can be manipulated to achieve a desired radial strength profile.

The radial strength decrease as a result in loss of molecule weight usually occurs only after a sustained period of patency (usually at least 3 months, pending the molecular structure and morphology) which allows for positive remodeling of the vessel wall. Thus, after the period of sustained patency, the vessel wall can maintain an increased mean lumen diameter, as shown by the mean lumen diameter.

Morphologically and functionally competent neointima/neomedia of the endothelial layer stabilizes scaffold and reduces thrombosis risk. Time for tissue stabilization is 4-5 months and for integrity loss is 6-9 months.

Controlled and gradual reduction of scaffolding strength and stiffness as function of time of the scaffold results in:
  reduction in compliance mismatch between the scaffold and native vessel with increased endoluminal deformability,
  an independent load-bearing integrated composite of the scaffold and native vessel (range of data cited—1.5 wk to 9 months),
  plaque fibrocellular capping and volume reduction (exhibit H).

With regard to plaque, the vessel wall includes a plaque region including a necrotic core component and a fibrocellular or fibrous component. As the scaffold degrades the fibrous component becomes positioned between the necrotic core component and the blood-contacting surface of the vessel wall so that the necrotic core component is not in contact with the blood-contacting surface, i.e., the necrotic core is capped by the fibrous component. There is also a reduction in volume of necrotic component as the scaffold degrades.

There are several possible metrics for cellular conduction and induction phenomena.

The first metric is the surface to volume (S/V) ratio of the scaffold. In general, it is believed that the S/V ratio of the scaffold influences the cellular growth over the scaffold. Specifically, it is believed that a high S/V favors cell deposition and growth on the scaffold. The surface can refer to the luminal surface, abluminal surface, side wall surfaces, or any combination thereof. It is further believed that the increase in S/V ratio generated due by strut discontinuities provides additional TE template and enhances or increases cell attachment and growth. When strut discontinuities are generated additional surface area is created at the discontinuities, which increases the S/V ratio. The number of strut discontinuities change with time, so the S/V metric is time dependent. The discontinuities at the links will enhance cell attachment and growth during the first three months after implantation while the scaffold provides patency. The discontinuities in the rings will further increase cell attachment and growth.

The volume of the scaffold changes with time also due to mass loss. The decrease in the volume as the scaffold degrades further contributes to the time dependence of the S/V metric.

Additionally, the S/V ratio with the bulk of the scaffold also changes with time. As a bulk-eroding polymer erodes, mass loss occurs throughout the volume of the scaffold which creates voids or pores throughout the volume of the scaffold. Therefore, the porosity of the scaffold increases with time, which increases the S/V ratio of the scaffold. The surface area within the scaffold provides a TE template for cell growth and attachment.

Another metric for cellular growth is the roughness of the scaffold surface. As the scaffold degrades, texture or roughness evolves on the stent surface due to mass loss. The evolution of this texture during degradation provides additional TE template. It is believed that the increase in surface area provided by such texture or roughness enhances cellular attachment and growth. Therefore, the roughness factor of the scaffold surface as a function of time is a metric for cellular growth.

An additional metric for cellular growth is the generation of degradation by products of the biodegradable polymer, such as PLLA. Specifically, degradation by products of a PLLA scaffold include low MW PLLA and lactic acid of the PLLA scaffold. Lactic acid and low MW PLLA have an inductive effect on tissue ingrowth and healing. Therefore distribution of MW(t) and lactic acid and low MW PLLA as a function of time are a metric.

The mechanical modulation and cellular conduction metrics of the disclosed scaffolds can facilitate clinically beneficial outcomes in the treatment of refractory lesions, bifurcated lesions, treatment of chronic total occlusion (CTO), vulnerable plaque (VP), left main, angulation, ostial, and multi-vessel treatment. Refractory lesions are typical in diabetic patients. Specifically, beneficial outcomes are facilitated by the gradual reduction in compliance mismatch with the vessel and the scaffold and reduction in chronic outward force with time. Additionally, beneficial outcomes are facilitated by the increase in cellular growth due to the increase in S/V, increase in roughness and induction in cell growth by degradation by-products. Further, beneficial outcomes are facilitated by capping of necrotic core plaque by fibrous plaque.

More specific examples of scaffolds, processes for making, fabricating and assembly the same, and observed outcomes (both in vivo and ex vivo) further explaining VRT principles and objectives follow.

Embodiments of processes for forming a deformed polymer tube from a precursor are provided. According to the disclosure, a crush recoverable and balloon expandable scaffold having time-varying properties is cut from a tube (FIG. 1) formed through a process intended to enhance mechanical properties of the scaffold including fracture toughness. Discussion of the scaffold patterns according to several embodiments are discussed next. Examples of the scaffold patterns are provided. During this discussion, reference is made to aspects of a scaffold found to play an important role in the stiffness, strength, crimping and deployment of a polymer scaffold. Finally, bench and in-vivo test results are discussed, including exemplary examples of embodiments of invention and explanation of the results observed and problems overcome. In these examples there may be gained a further appreciation of aspects of invention—a balloon-expandable polymer scaffold having time-varying properties for purposes of achieving a desired Input A to the VRT process—and examples of processes including sample M parameters for predicting, assessing and improving upon a scaffold's fitness for use in a peripheral vessel.

Figure 2:
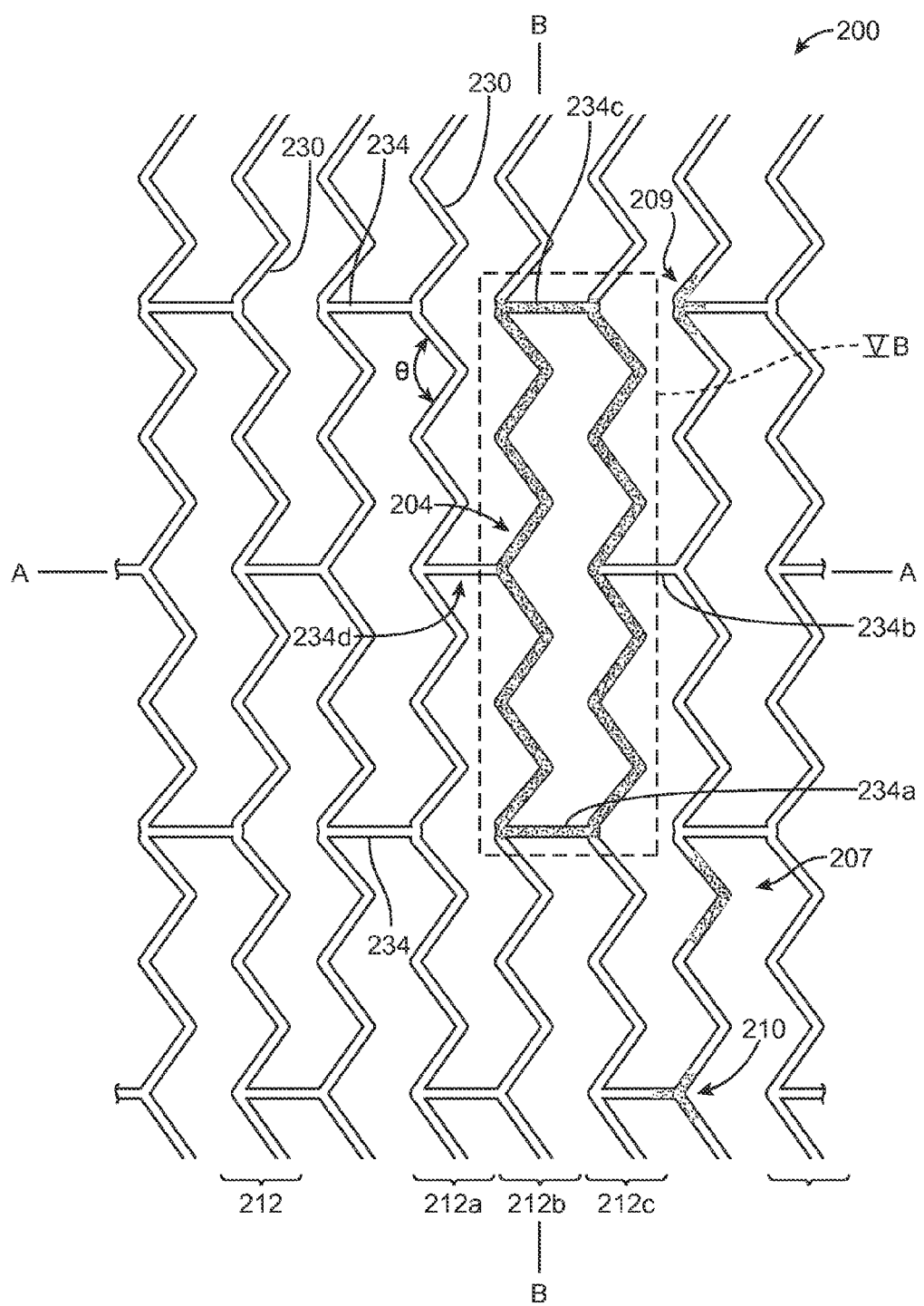
FIG. 2 is a partial planar view of a scaffold pattern according to a first embodiment of a scaffold.

The polymer scaffold illustrated in FIG. 2 is formed from a poly(L-lactide) ("PLLA") tube. The process for forming this PLLA tube may be the process described in U.S. patent application Ser. No. 12/558,105. Reference is made to a precursor that is "deformed" in order to produce the tube of FIG. 1 having the desired scaffold diameter, thickness and material properties as set forth below. Before the tube is deformed or, in some embodiments, expanded to produce the desired properties in the starting tube for the scaffold, the precursor is formed. The precursor may be formed by an extrusion process which starts with raw PLLA resin material heated above the melt temperature of the polymer which is then extruded through a die. Then, in one example, an expansion process for forming an expanded PLLA tube includes heating a PLLA precursor above the PLLA glass transition temperature (i.e., 60-70 degrees C.) but below the melt temperature (165-175 degrees C.), e.g., around 110-120 degrees C.

A precursor tube is deformed in radial and axial directions by a blow molding process wherein deformation occurs progressively at a predetermined longitudinal speed along the longitudinal axis of the tube. As explained below, the deformation improves the mechanical properties of the tube before it is formed into the scaffold of FIG. 2. The tube deformation process is intended to orient polymer chains in radial and/or biaxial directions. The orientation or deformation causing re-alignment is performed according to a precise selection of processing parameters, e.g. pressure, heat (i.e., temperature), deformation rate, to affect material crystallinity and type of crystalline formation during the deformation process.

In an alternative embodiment the tube may be made of poly(L-lactide-co-glycolide), poly(D-lactide-co-glycolide) ("PLGA"), polycaprolactone, ("PCL"), any semi-crystalline copolymers combining any of these monomers, or any blends of these polymers. Material choices for the scaffold should take into consideration the complex loading environment associated with many peripheral vessel locations, particularly those located close to limbs. Examples are described in U.S. patent application Ser. No. 13/525,145.

The femoral artery provides a dynamic environment for vascular implants as various forces may crush, twist, extend, or shorten the device simultaneously. The force application may vary between point load to distributed load or a combination thereof and also as a function of time. Recent results have shown that bioresorbable scaffolds made from highly crystalline PLLA can provide crush recovery without causing a permanent and constant outward radial force on the vessel. The permanent and constant outward radial force may be the cause of late clinical issues with nitinol self-expandable stents. However, a remaining challenge with bioresorbable scaffolds is to make them optimally fracture resistant as a function of time; that is, to improve their fatigue life or survivability under a variety of dynamic loading environments. There is a continuing need to improve fracture toughness for a scaffold; and in particular a peripherally implanted scaffold.

The fracture resistance of a vascular scaffold depends not only on the design and the material, but is also the manufacturing process and deployment parameters. Therefore it is in particular necessary to have a process, design, and a delivery system that allows the scaffold to be uniformly expanded and deployed. As a consequence of non-uniform deployment the various struts and crowns of a scaffold will potentially be exposed to very different forces and motions, which has a deleterious effect on the fatigue life.

Alternative ways to improve the fatigue properties are through introduction of axial flexibility and the use of pre-designed fracture points, in particular in the connector links. The fracture points could function as precursors of actual fractures, e.g., crazes and cracks or small dimension of fracture distributed in the implant. A distribution or pattern of cracks or crazes may dictate or inform one of an expected toughness of the scaffold when subjected to a particular loading, e.g., torsion, radial force, tensile etc. Although it is understand that, due to the generally highly non-linear relationship between crack formation and a coupled loading environment, that is, simultaneously applied and time varying bending, torsion and axial loading, such predictive methods may not be applicable to all situations.

Alternative ways to improve the fatigue properties are through introduction of axial flexibility and the use of pre-designed fracture points, in particular, fracture points in or near connector links as discussed in greater detail below.

For a tube of FIG. 1 having a diameter about 7 mm and a wall thickness above 200 micro-meters and more specifically a diameter of 8 mm and a wall thickness of 280 micro-meters, the temperature at expansion is 235+/−5 degrees Fahrenheit, the expansion pressure is 110+/−10 psi and the expansion speed is 0.68+/−0.20 mm/sec. The degree of radial expansion that the polymer tube undergoes can partially characterize the degree of induced circumferential molecular and crystal orientation as well as strength in a circumferential direction. In some embodiments the RE is about 400% and the AE is 40-50%. Other embodiments of processing parameters, RE and AE expansions considered within the scope of the disclosure are found in U.S. application Ser. No. 13/840,257 filed Mar. 15, 2013.

Figure 3:
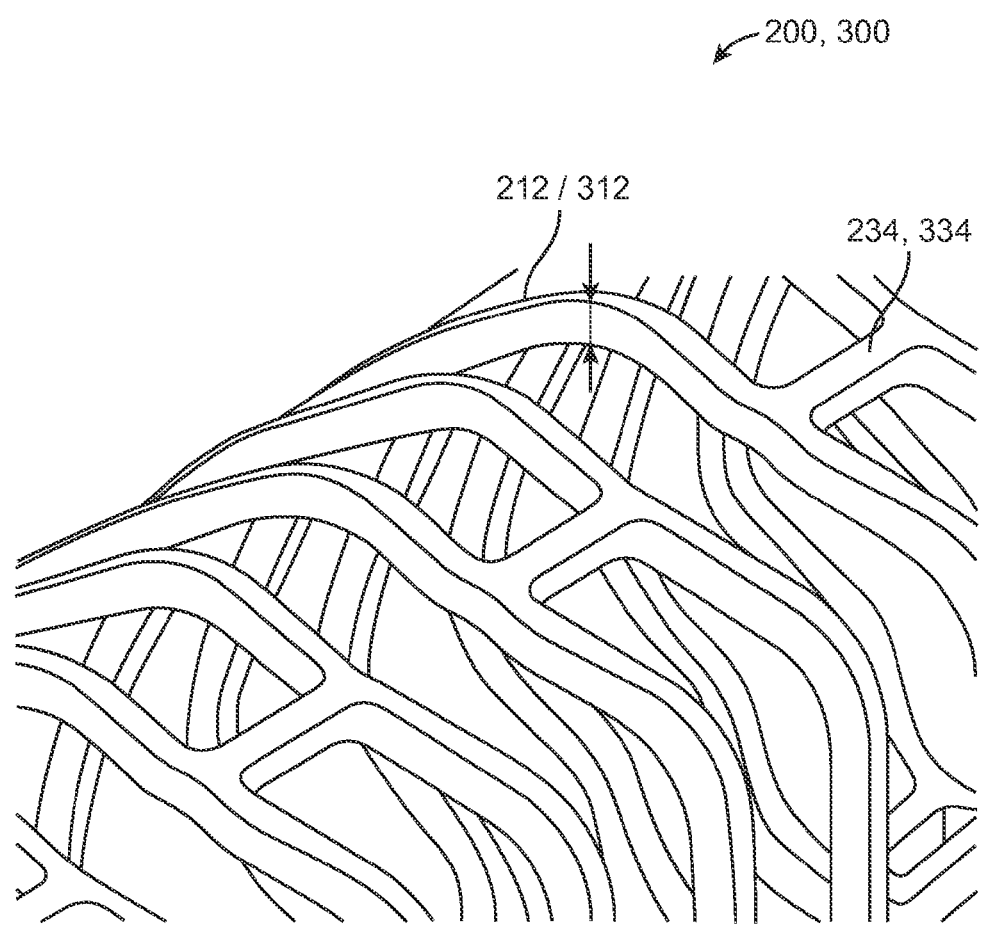
FIG. 3 is a partial perspective view of a scaffold structure.

The strengthened and toughened cylindrical, polymer tube of FIG. 1 is formed into a scaffold structure, in one embodiment a structure having a plurality of struts 230 and links 234 forming a pattern 200 as shown in FIG. 2 (pattern 200 is illustrated in a planar or flattened view), which is about the pattern for the scaffold before crimping and after the scaffold is plastically, or irreversibly deformed from its crimped state to its deployed state within a vessel by balloon expansion. The pattern 200 of FIG. 2, therefore, represents a tubular scaffold structure (as partially shown in three dimensional space in FIG. 3), so that an axis A-A is parallel to the central or longitudinal axis of the scaffold. FIG. 3 shows the scaffold in a state prior to crimping or after deployment. As can be seen from FIG. 3, the scaffold comprises a framework of struts and links that define a generally tubular body. The cylindrical, deformed tube of FIG. 1 may be formed into this open framework of struts and links described in FIGS. 2-3 by a laser cutting device, preferably, a pico-second green light laser that uses Helium gas as a coolant during cutting.

Referring to FIG. 2, the pattern 200 includes longitudinally-spaced rings 212 formed by struts 230. There are eight crests formed by the struts. A ring 212 is connected to an adjacent ring by no more than two links 234, each of which extends parallel to axis A-A. In this first embodiment of a scaffold pattern (pattern 200) two links 234 connect the interior ring 212, which refers to a ring having a ring to its left and right in FIG. 2, to each of the two adjacent rings. Thus, ring 212b is connected by two links 234 to ring 212c and two links 234 to ring 212a. An end ring (not shown) is an end ring connected to only one other ring.

A ring 212 is formed by struts 230 connected at crowns 207, 209 and 210. A link 234 is joined with struts 230 at a crown 209 (W-crown) and at a crown 210 (Y-crown). A crown 207 (free-crown) does not have a link 234 connected to it. Preferably the struts 230 that extend from a crown 207, 209 and 210 at a constant angle from the crown center, i.e., the rings 212 are approximately zig-zag in shape, as opposed to sinusoidal for pattern 200. As such, in this embodiment a ring 212 height, which is the longitudinal distance between adjacent crowns 207 and 209/210 may be derived from the lengths of the two struts 230 connecting at the crown and a crown angle $\ominus$. In some embodiments the angle $\ominus$ at different crowns will vary, depending on whether a link 234 is connected to a free or unconnected crown, W-crown or Y-crown.

The zig-zag variation of the rings 212 occurs primarily about the circumference of the scaffold (i.e., along direction B-B in FIG. 2). The struts 212 centroidal axes lie primarily at about the same radial distance from the scaffold's longitudinal axis. Ideally, substantially all relative movement among struts forming rings also occurs axially, but not radially, during crimping and deployment. Although, as explained in greater detail, below, polymer scaffolds often times do not deform in this manner due to misalignments and/or uneven radial loads being applied.

The rings 212 are capable of being collapsed to a smaller diameter during crimping and expanded to a larger diameter during deployment in a vessel. According to one aspect of the disclosure, the pre-crimp diameter (e.g., the diameter of the axially and radially expanded tube from which the scaffold is cut) is always greater than, or equal to a maximum expanded scaffold diameter that the delivery balloon can, or is capable of producing when inflated.

Figure 4:
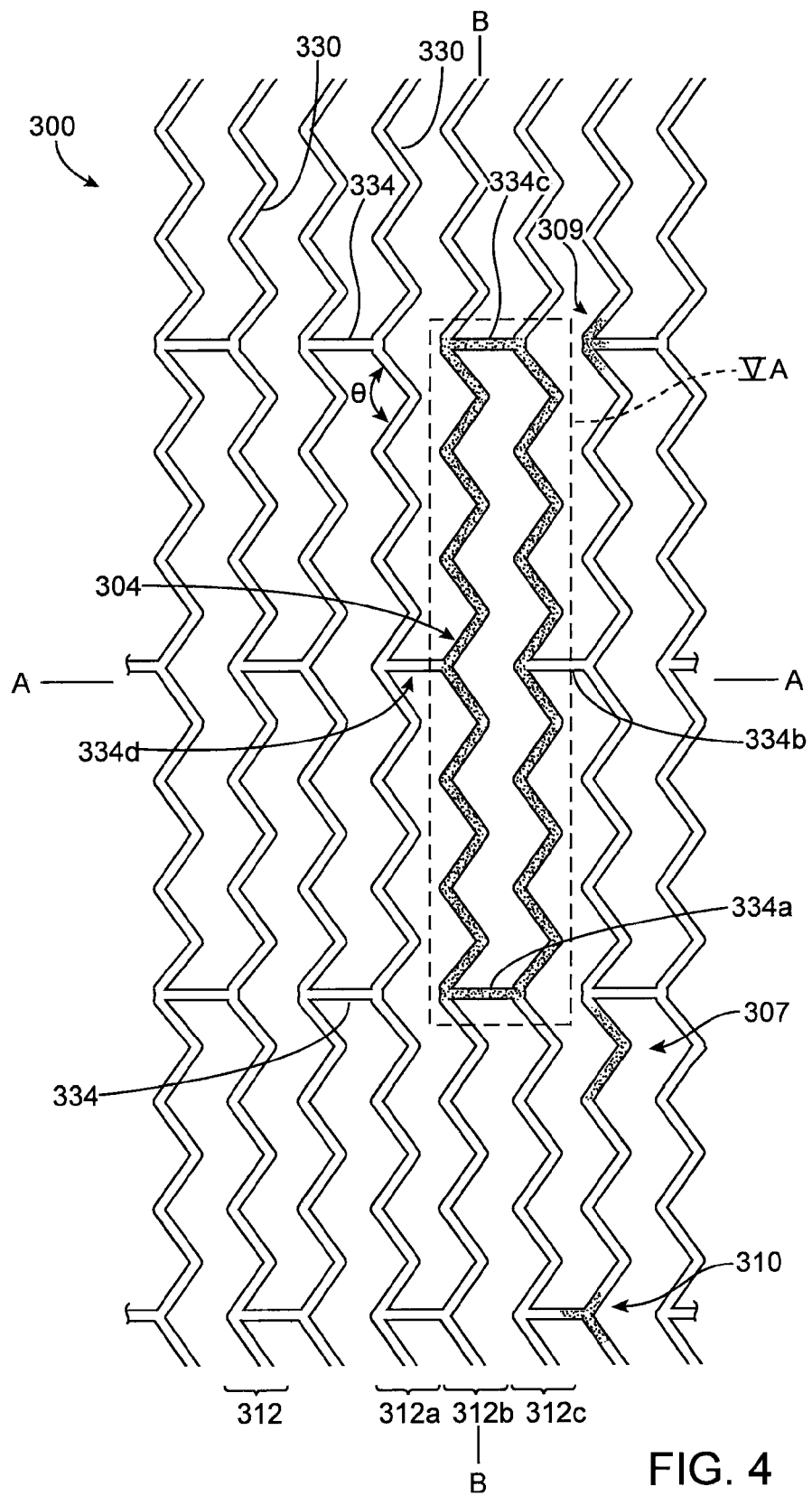
FIG. 4 is a partial planar view of a scaffold pattern according to a second embodiment of a scaffold.

A second embodiment of a scaffold structure has the pattern 300 illustrated in FIG. 4. Like the pattern 200, the pattern 300 includes longitudinally-spaced rings 312 formed by struts 330. There are twelve crests formed by the struts for each ring 312. A ring 312 is connected to an adjacent ring by no more than two links 334, each of which extends parallel to axis A-A. The description of the structure associated with rings 212, struts 230, links 234, and crowns 207, 209, 210 in connection with FIG. 2, above, also applies to the respective rings 312, struts 330, links 334 and crowns 307, 309 and 310 of the second embodiment, except that in the second embodiment there are 12, as opposed to 8 crests for each ring 312 for pattern 300.

Figure 5A:
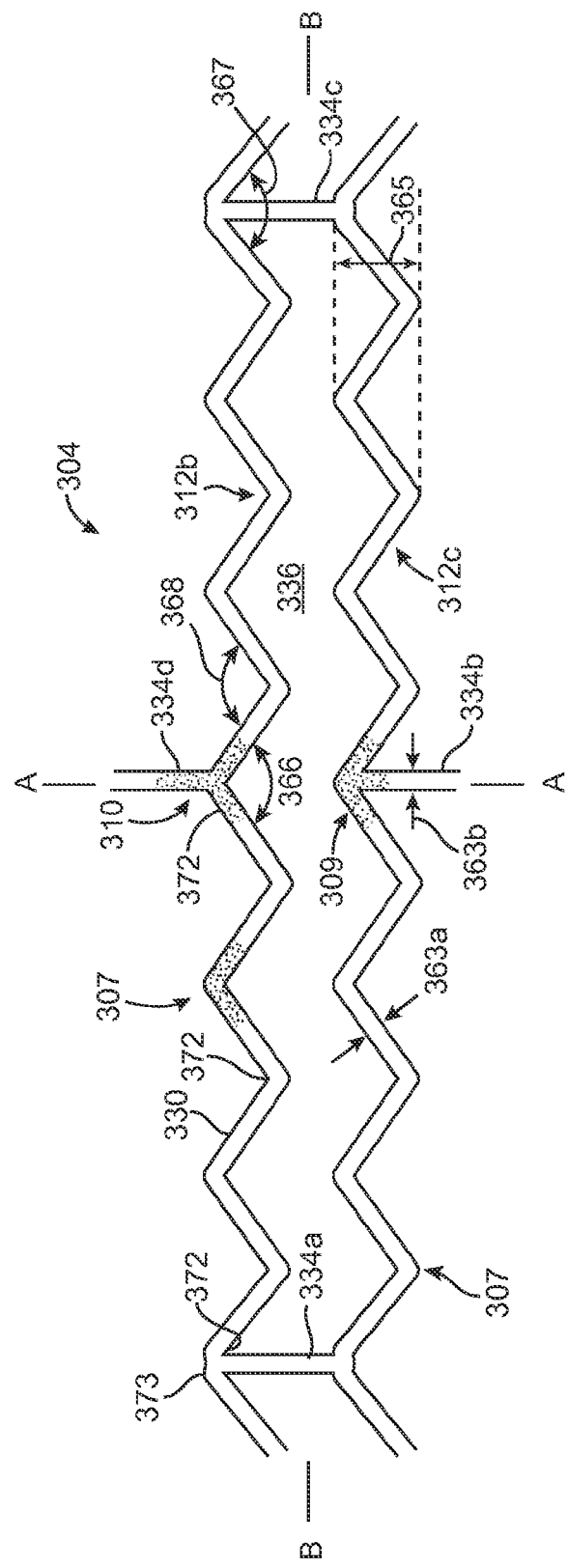
FIG. 5A is a planar view of the portion VA of the scaffold pattern of FIG. 4.
Figure 5B:
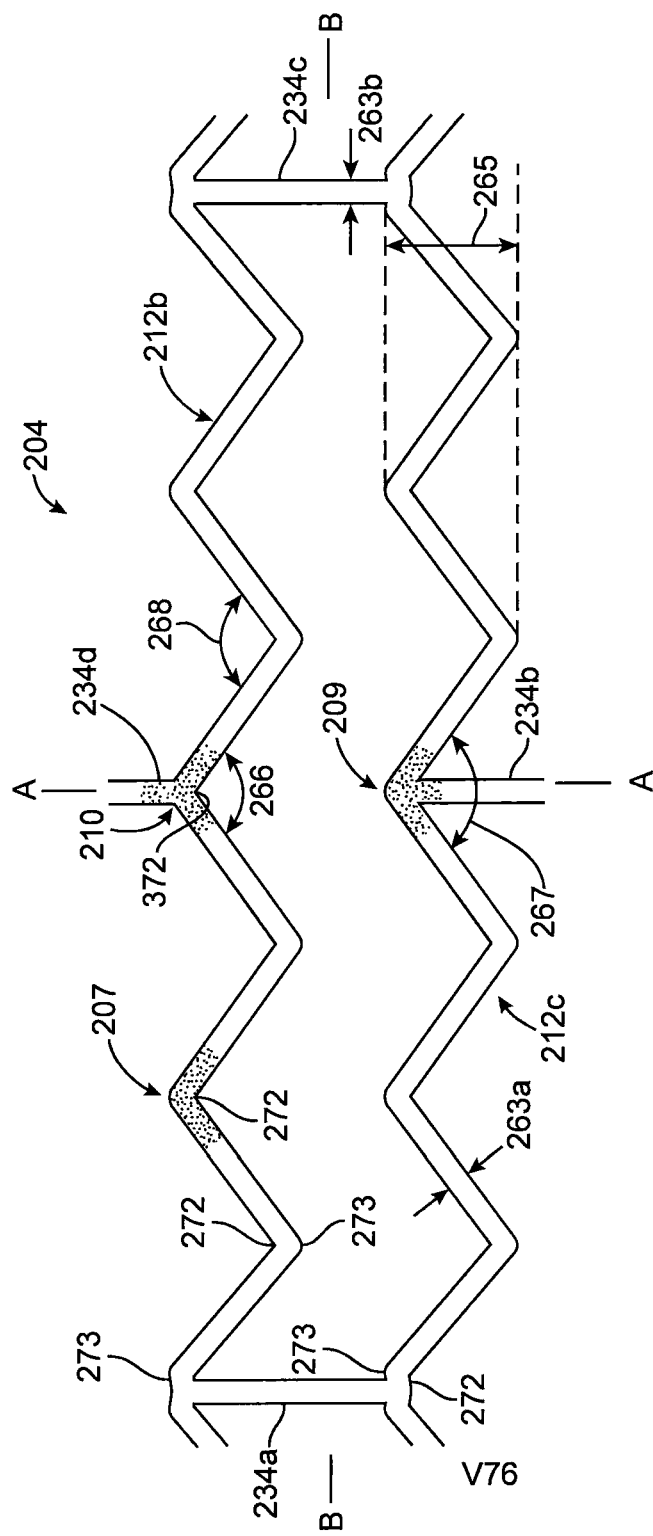
FIG. 5B is a planar view of the portion VB of the scaffold pattern of FIG. 2.

FIGS. 5A and 5B depict aspects of the repeating pattern of closed cell elements associated with each of the patterns 300 and 200, respectively. FIG. 5A shows the portion of pattern 300 bounded by the phantom box VA and FIG. 5B shows the portion of pattern 200 bounded by the phantom box VB. Therein are shown cell 304 and cell 204, respectively. In FIGS. 5A, 5B the vertical axis reference is indicated by the axis B-B and the longitudinal axis A-A. There are two such cells 204 formed by each pair of rings 212 in pattern 200, e.g., two cells 204 are formed by rings 212b and 212c and the links 234 connecting this ring pair, another two cells 204 are formed by rings 212a and 212b and the links connecting this ring pair, etc. Similarly, there are two cells 304 formed by rings 312b and 312c and the links 334 connecting this ring pair, another two cells 304 are formed by rings 312a and 312b and the links connecting this ring pair, etc.

Referring to FIG. 5A, the space 336 of cell 304 is bounded by the longitudinally spaced rings 312b and 312c portions shown, and the circumferentially spaced and parallel links 334a and 334c connecting rings 312b and 312c. Links 334b and 334d extend parallel to each other and connect the cell 304 to the right and left adjacent ring in FIG. 4, respectively. Link 334b connects to cell 304 at a W-crown 309. Link 334d connects to cell 304 at a Y-crown 310. A "W-crown" refers to a crown where the angle extending between a strut 330 and the link 334b at the crown 309 is an acute angle (less than 90 degrees). A "Y-crown" refers to a crown where the angle extending between a strut 330 and the link 334d at the crown 310 is an obtuse angle (greater than 90 degrees). The same definitions for Y-crown and W-crown also apply to the cell 204. There are eight crests formed as unconnected or "U-crowns" 307 for cell 304, which may be understood as eight crests devoid of a link 334 connected at the crest. There are always two crests formed as U-crowns between a crest formed as a Y-crown or W-crown for the cell 304.

Additional aspects of the cell 304 of FIG. 5A include angles for the respective crowns 307, 309 and 310. Those angles are identified in FIG. 6A. For the scaffold having the pattern 300 the struts 330 have strut widths 363a, and the links 334 have widths 363b. Each of the rings 312 has a ring height 365. The radii at the crowns are, in general, not equal to each other. The radii of the crowns are identified in FIG. 6A. Cell 304 of pattern 300 may be regarded as a symmetric cell, by virtue of it always having two U-crowns on each side of a W-crown and Y-crown as shown.

Referring to FIG. 5B, cell 204 is bounded by the portions of longitudinally spaced rings 212b and 212c as shown, and the circumferentially spaced and parallel links 234a and 234c connecting these rings. Links 234b and 234d connect the cell 204 to the right and left adjacent rings in FIG. 2, respectively. Link 234b connects to cell 204 at a W-crown 209. Link 234d connects to cell 204 at a Y-crown 210. There are four crests formed as crowns 207 for cell 204, which may be understood as four crests devoid of a link 234 connected at the crest. Cell 204 may also be regarded as a symmetric cell, by virtue of it always having one crest formed as a U-crown on each side of a crest formed as a W-crown or Y-crown as shown.

Additional aspects of the cell 204 of FIG. 5B include angles for the respective crowns 207, 209 and 210. Those angles are identified in FIG. 5B as angles 267, 269 and 268, respectively associated with crowns 207, 209 and 210. For the scaffold having the pattern 200 the struts 230 have strut widths 263a, crowns 207, 209, 210, and the links 234 have link widths 263b. Each of the rings 212 has a ring height 265. The radii of the crowns are identified in FIG. 5B as inner radii 272 and outer radii 273.

The V76 and V80 both have a symmetric cell design. A "symmetric" cell design (as shown in FIGS. 5A and 5B) has an equal number of U-crowns on each side of a W-crown or Y-crown. An example of an asymmetric cell design would be the V23 scaffold pattern, as described in US2011/0190871.

A significant difference between the V80 and V76 is that the V76 (as well as other designs, described below) has eight crests and two links whereas the V80 design has twelve crests and two links. Having more crowns and therefore shorter bar arms than other designs, the V80 has a higher density of struts. For example, a 60 mm V80 scaffold has 33 rings and a total of 396 ring struts/scaffold, which can be compared to a total of 216 ring struts (27 rings×8 struts per ring)/scaffold for the V76 design, and 200 ring struts/scaffold for the V59. In-vivo tests show that with a higher density of struts there is a lower late lumen loss for the V80.

Crimping of the scaffold, as detailed in U.S. application Ser. No. 13/194,162, includes heating the polymer material to a temperature less then, but near to the glass transition temperature of the polymer. In one embodiment the temperature of the scaffold during crimping is raised to about 5 to 10 degrees below the glass transition temperature for PLLA. When crimped to the final, crimped diameter, the crimping jaws are held at the final crimp diameter for final dwell period. This method for crimping a polymer scaffold having crush recovery is advantageous to reduce recoil when the crimp jaws are released. After the final dwell period, the scaffold is removed from the crimper and a constraining sheath is immediately placed over the scaffold to minimize recoil. Examples of such a sheath are described in US20120302955.

Testing of Scaffold Designs

TABLE 3 provides a summary of the characteristics of various scaffolds that were tested in in-vitro and in-vivo to evaluate and compare various performance characteristics, as described in FIGS. 7-22 and the description that follows.

TABLE 3

| | scaffold types | | | | |
|---|---|---|---|---|---|
| | | | Pattern | | |
| Scaffold Type | Wall thickness (in) | Tube OD (mm) | Number of crests or troughs | Links connecting adjacent rings | material |
| S-1, S-2 | see U.S. application Ser. No. 13/252,121 (docket no. 104584.22) | | | | |
| V2 | .008 | 7 | 9 | 3 | PLLA |
| V23-008 | .008 | 7 | 9 | 3 | PLLA |
| V23-014 | .014 | 9 | 9 | 3 | PLLA |
| V59 | .011 | 8 | 8 | 4 | PLLA |
| V62 | .011 | 7 | 9 | 3 | PLLA |
| V76 | .011 | 7 | 8 | 2 | PLLA |
| V78 | .011 | 7 | 8 | 2 | PLLA |
| V79 | .011 | 7 | 8 | 2 | PLLA |
| V79 - PLCL90/10 | .011 | 8 | 8 | 2 | PLLA-PCL (90/10) |
| V80 | .011 | 7 | 12 | 2 | PLLA |

FIGS. 7-15 show results from various in-vitro tests, which were used to compare the mechanical properties of the V76 and V62 scaffolds to the V59 scaffold (see US2011/0190871 for full description of the V59). These tests were directed towards determining the radial strength and/or stiffness, acute recoil, crush recovery, pinching stiffness, and fatigue or fracture of the scaffold after repeated loading of the scaffold.

The scaffolds were crimped to about a 0.085 in outer diameter (within the crimper head), sterilized by E-beam radiation, then expanded to 6.4 mm outer diameter using a 6.0 mm balloon prior to initiating the tests. The scaffold were made from PLLA and cut from a biaxial expanded tube using the process described earlier. Tests were conducted to assess the fracture toughness or number of discontinuous, cracked or broken struts appearing in the V59, V62 and V76 scaffolds under different test conditions.

Figure 7:
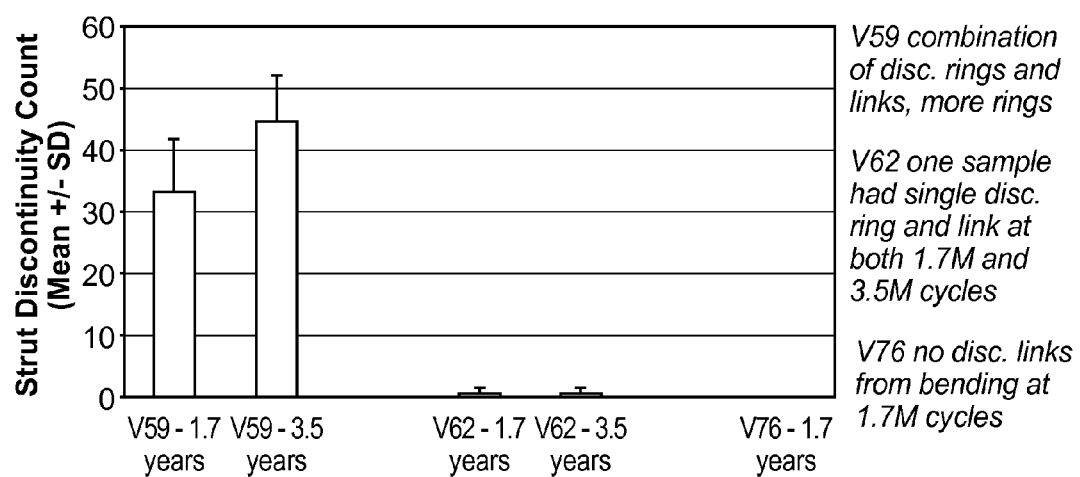
FIG. 7 compares results from a bending fatigue test among the V76, V62 and V59 scaffolds.

FIG. 7 compares results from a bending fatigue test between the V59, V62 and V76 scaffolds. For the three-point bending test and the bending fatigue test the bending axis is considered to be random, i.e., the statistical results depict the fatigue data for a bending axis about any axis passing through and perpendicular to the bending axis of the scaffold.

Figures 8, 9:
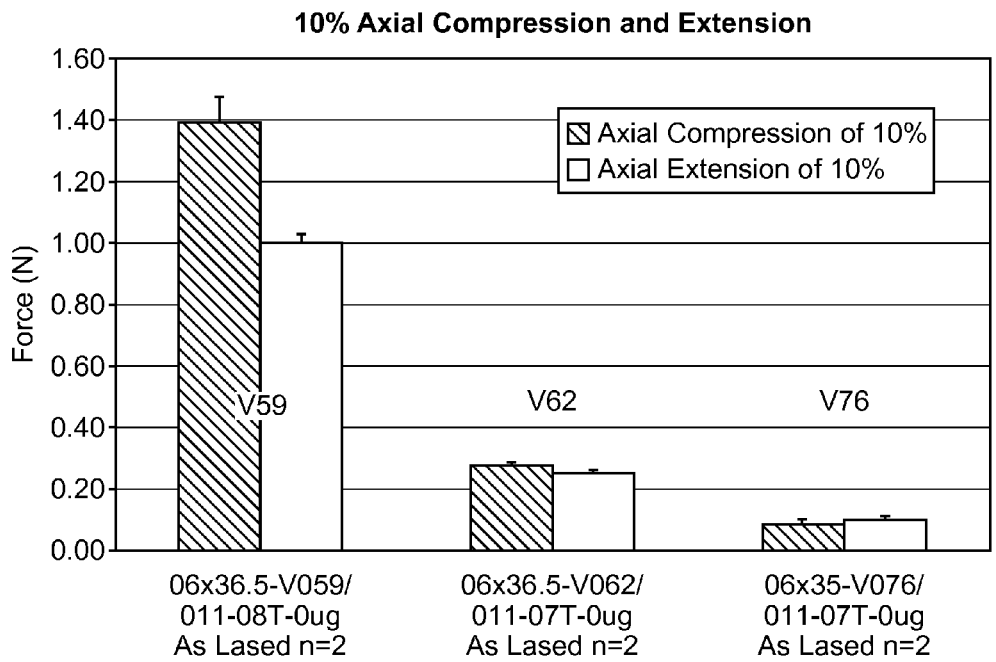
FIG. 8 compares the axial force among the V76, V62 and V59 scaffolds for a 10% static compression and extension.
FIG. 9 shows a mean and standard deviation fractures at crowns and links for the V76 scaffold for one month and six month simulated walking tests of the V76.

FIG. 8 compares the axial force for a 10% static compression and extension of the V76 scaffold compared to the V59 and V62 scaffolds.

FIG. 9 is a table showing the mean and standard deviation fractures at crowns and links for the V76 scaffold for one month and six month simulations of axial loading of the V76 scaffold when implanted within the femoral artery. For these tests the V76 scaffold was subjected to a 7% axial compression and extension at 37 degrees Celsius within a loaded silicon tubing simulating axial loading of the femoral artery.

Figure 10:
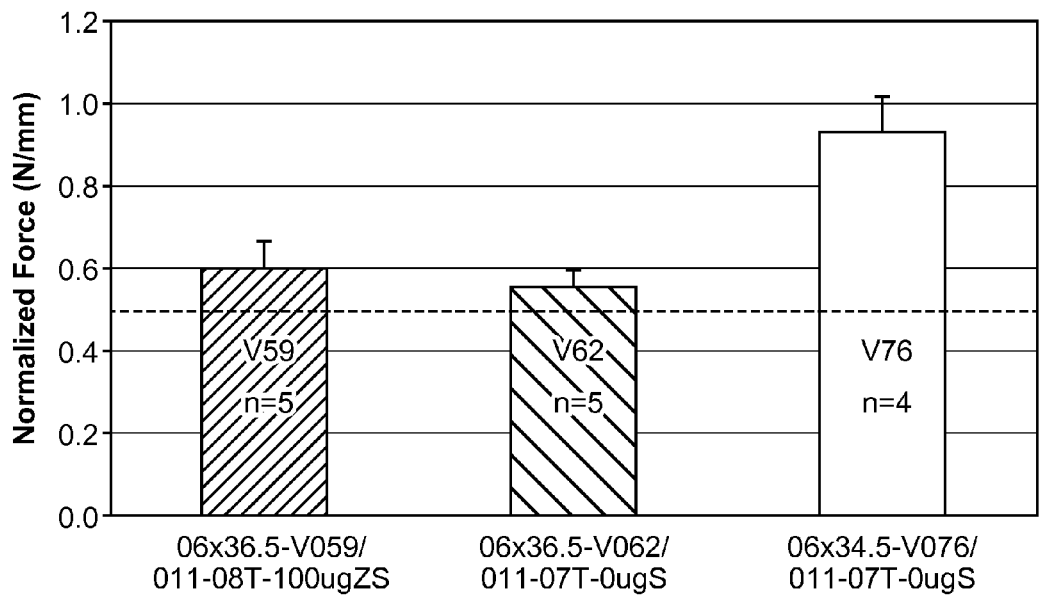
FIG. 10 compares the radial strength among the V76, V62 and V59 scaffolds.
Figure 11:
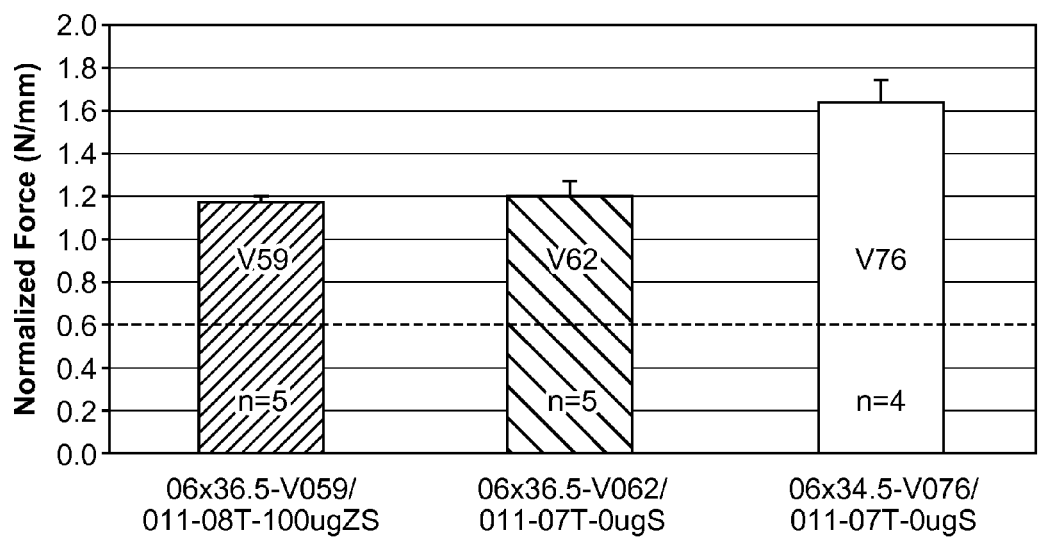
FIG. 11 compares the radial stiffness among the V76, V62 and V59 scaffolds.

FIG. 10 compares the radial strength of the V76 and V62 scaffolds to the V59 scaffold.

Figures 12, 13:
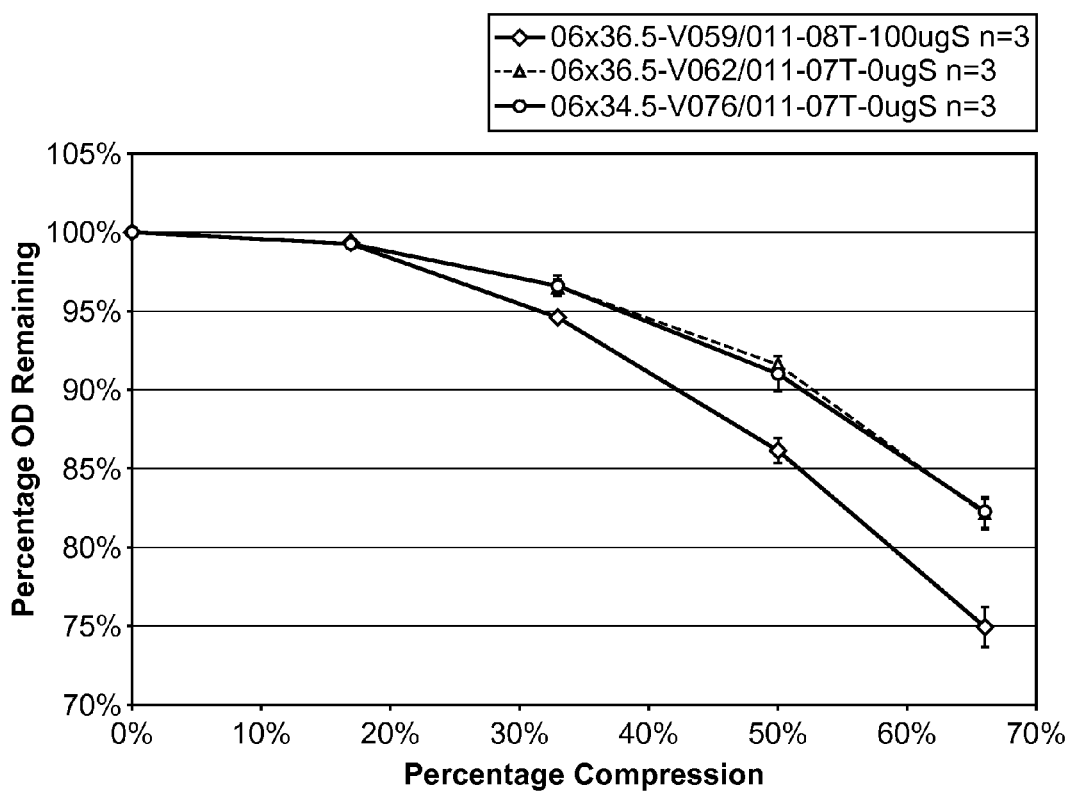
FIG. 12 compares the acute recoil of the V76 scaffold to the V59 and V62 scaffold, and the V2 scaffold described in WO2011094621.
FIG. 13 compares the crush-recovery among the V76, V62 and V59 scaffolds.

FIG. 12 compares the radial stiffness of the V76 and V62 scaffolds to the V59 scaffold.

FIG. 13 compares the acute recoil of the V76 scaffold to the V59, V2 (as described in US2011/0190871) and V62 scaffolds.

FIG. 13 compares the crush-recovery of the V76 scaffold to the V59 scaffold and V62 scaffolds.

Figure 14:
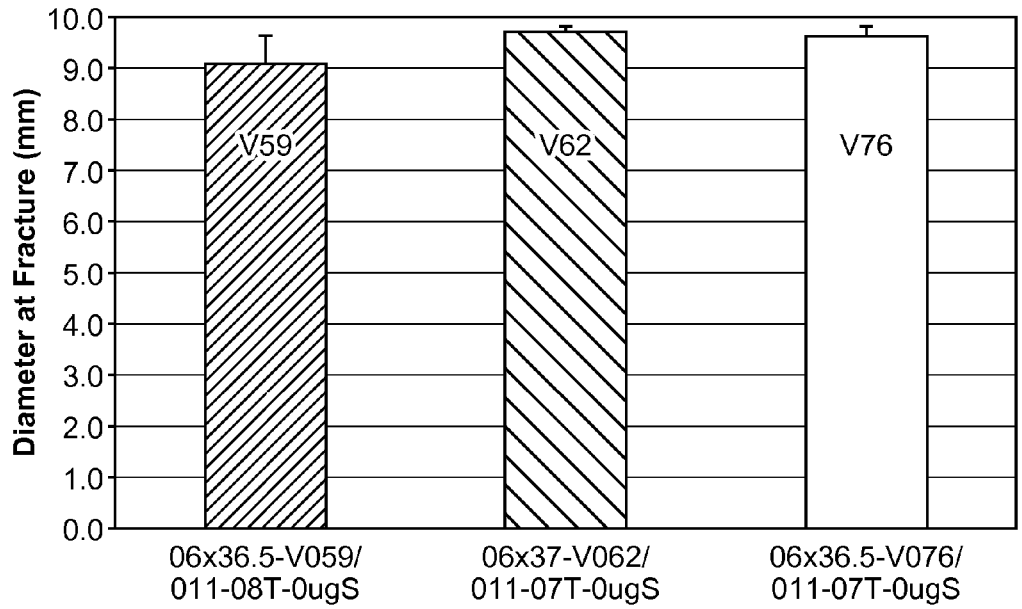
FIG. 14 compares the deploy-to-fracture among the V76, V62 and V59 scaffolds. This plot shows that the V76 begins to develop critical fractures at a higher diameter than the V59.
Figure 16:
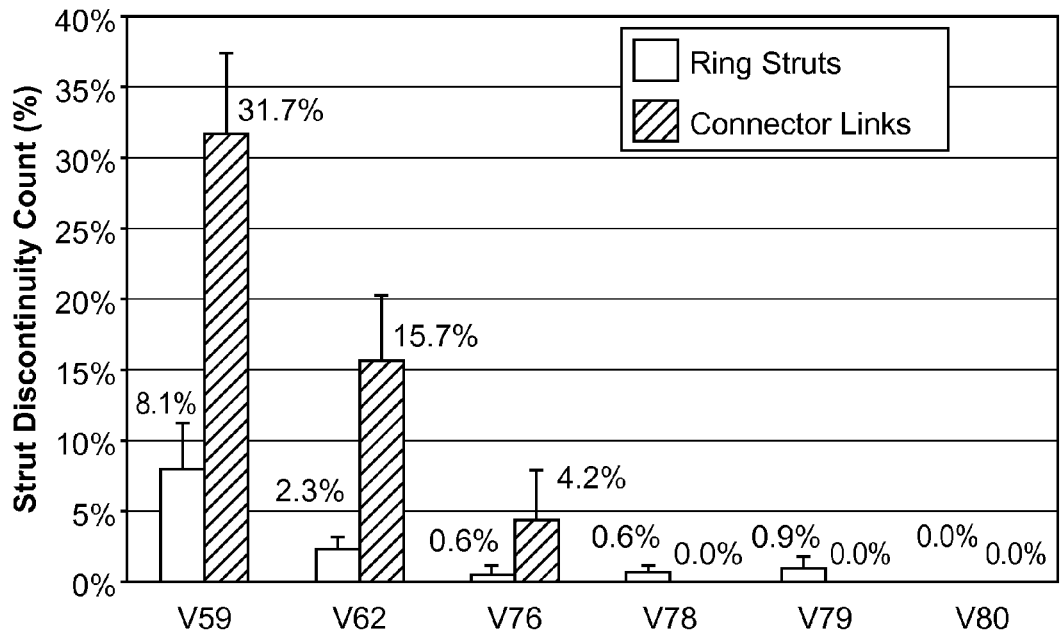
FIG. 16 compares the percentage of discontinuities, fractures or failures of struts and links among several scaffold designs having different numbers of crowns and/or links connecting ring structures. The discontinuities are counted following a six-month simulated walking test.

FIG. 14 compares the deploy-to-fracture of the V76 scaffold to the V59 scaffold and V62 scaffolds. This plot shows that the V76 begins to develop critical fractures at a higher diameter than the V59. FIG. 16 compares the pinching stiffness of the V76 scaffold to the V59 scaffold and V62 scaffolds.

FIG. 16 shows the total percentage of discontinuity (cracked or broken struts and links) for the V59, V62, V76, V78, V79 and V80 scaffolds after 500,000 cycles of 7% axial compression of the scaffold (equivalent to 6-month walking).

In-Vivo Testing

Figure 18:
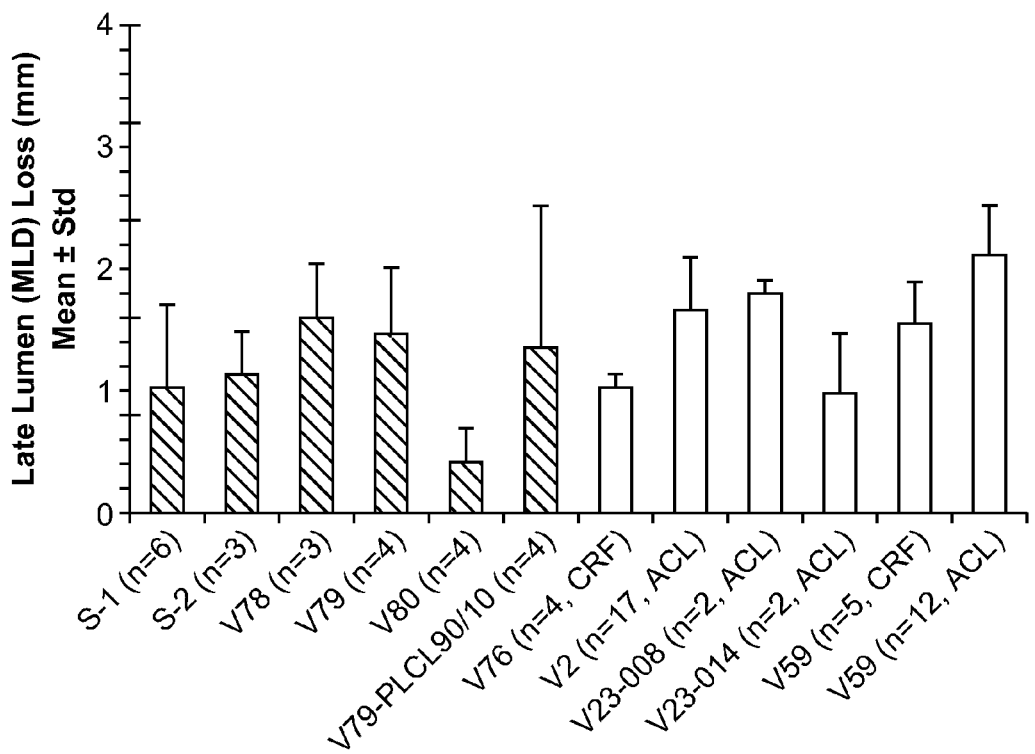
FIG. 18 compares the in-vivo late lumen loss among several scaffold designs after 28 days implantation.
Figure 19:
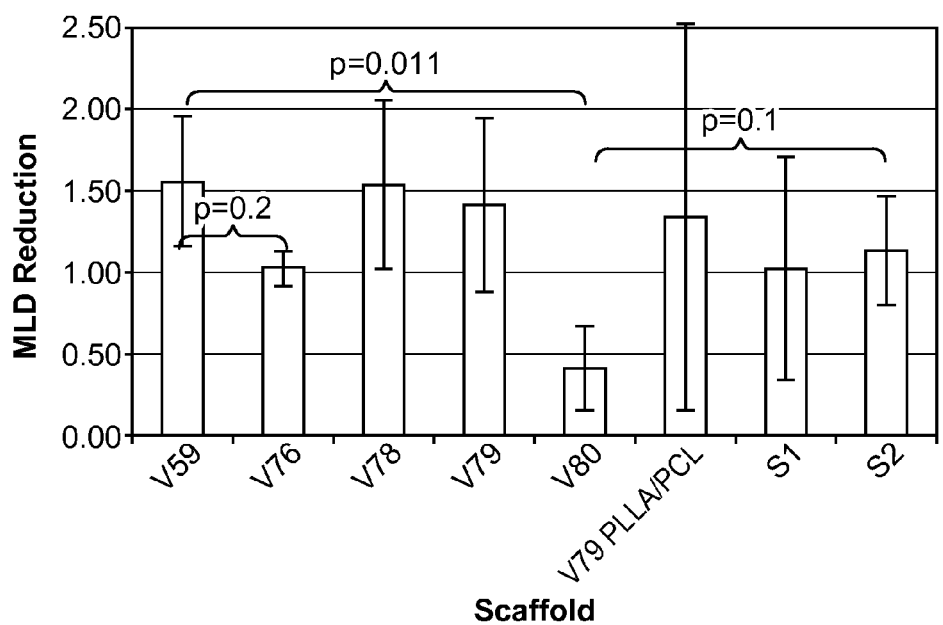
FIG. 19 provides statistical significance values (t-test) for the late lumen loss in FIG. 18.
Figure 20:
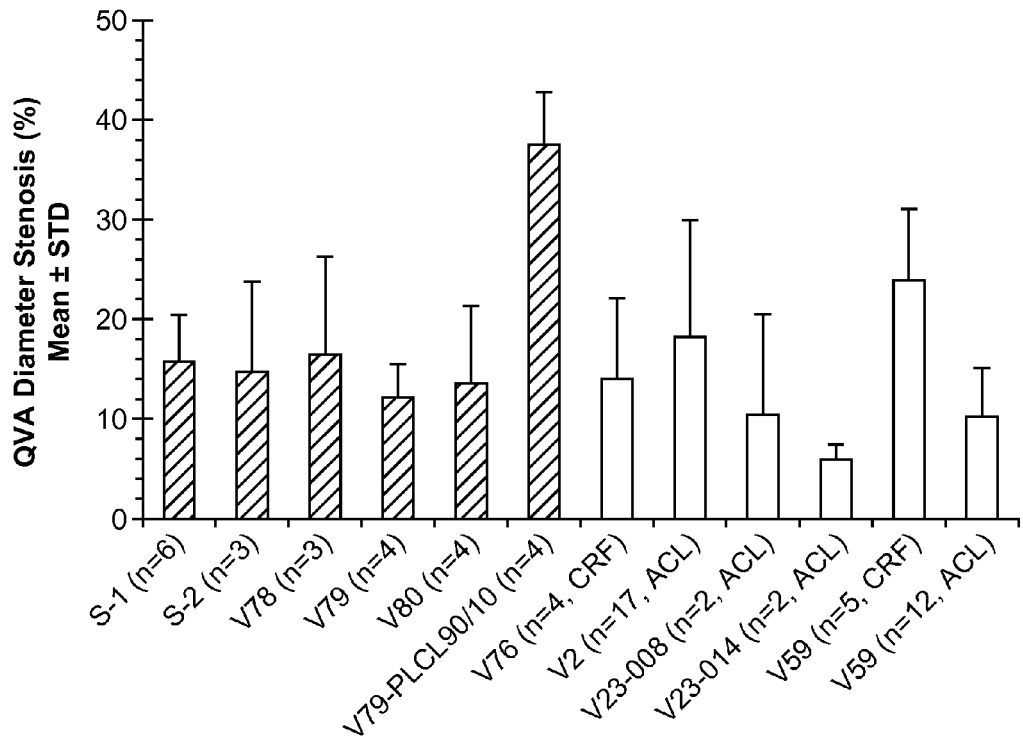
FIG. 20 compares the percentage diameter stenosis 28 days following implantation for different scaffolds.

FIGS. 18-20 compares minimum lumen diameter (MLD) or late loss and percentage of stenosis following a 28 day implant for each of the scaffold in TABLE 1. Each scaffold was implanted into the iliofemoral artery of a healthy porcine model and after 28 days explants were obtained in order to evaluate and compare the effectiveness of the polymer scaffolds in maintaining vascular patency. The implanted scaffolds were subject to various degrees of hip extension and flexion by the swine, which is believed to impose about 90 degrees bending, and about 3-15% axial compression of the implanted scaffold during a maximum hip and knee flexion.

The scaffold were crimped to about a 0.085 in outer diameter (within the crimper head), sterilized by E-beam radiation, introduced into the animal model using standard procedures, then expanded within the artery to a 6.4 mm outer diameter using a 6.0 mm balloon. The scaffold were made from PLLA (exc. V79 PLLA-PCL) and cut from a biaxial expanded tube using the process described earlier.

The data in FIGS. 18-20 were obtained using Quantitative Vascular Analysis (QVA) to determine the MLD and stenosis %. The number "n" in the figures represents the number of explants that were used to arrive at the mean and standard deviation values provide in FIGS. 18-20.

Figure 17:
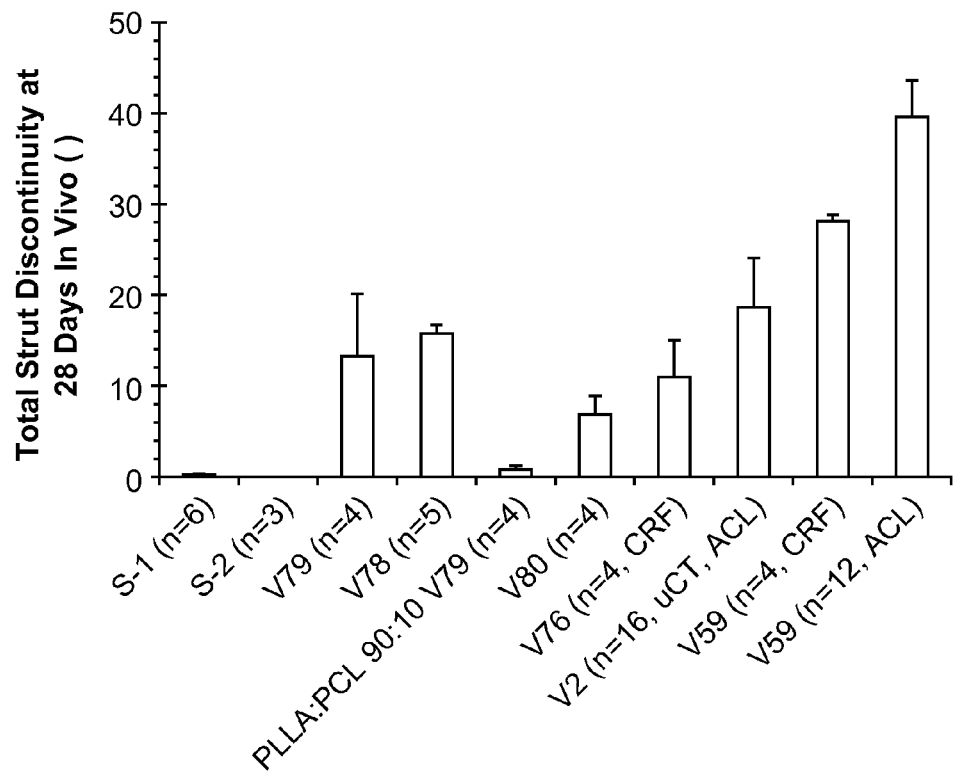
FIG. 17 counts the total number of discontinuities, fractures or failures of struts and links among the several scaffold designs from FIG. 16, 28 days after being implanted in the animal model.

FIG. 17 counts the total number of strut discontinuities found in the explants for the V59, V62, V76, V79 and V80 scaffolds.

FIG. 18 compares the late lumen loss or minimum lumen diameter (MLD) in the explants for the V59, V62, V76, V79 and V80 scaffolds.

FIG. 19 shows late lumen loss from FIG. 18 with statistical significance indicated between scaffolds. There is a significant p value of 0.011 (t-test) for the V80 scaffold data compared to the V59 scaffold data. Tables 2A and 2B, below, provides a summary of characteristics of the scaffolds. "ACL" and "CRF" indicate different locations for the in-vivo tests.

TABLE 4A performance characteristics for scaffold types in TABLE 2

Figure 15:
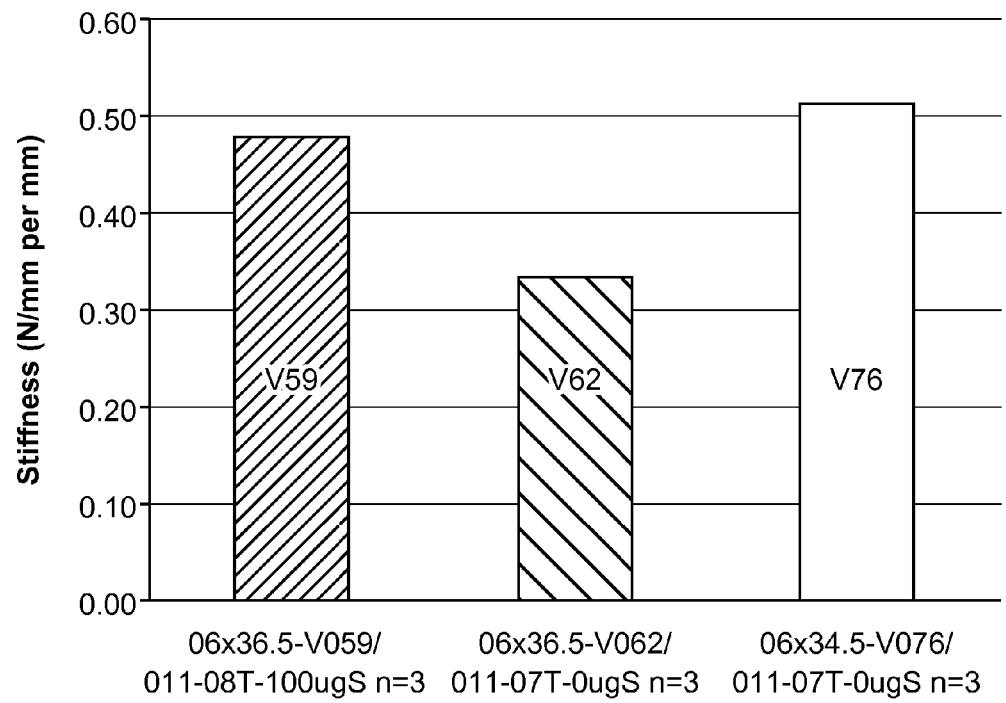
FIG. 15 compares the pinching stiffness among the V76, V62 and V59 scaffolds.

| Scaffold Type | Stenosis (28 days) (%) FIG. 20 | Late Lumen loss (28 days) (mm) FIG. 18 | Axial Fatigue % (6 months) struts FIG. 16 | Axial Fatigue % (6 months) Links FIG. 16 | Stiffness (N/mm) FIG. 15 | In vivo % fracture (28 days) FIG. 17 |
|---|---|---|---|---|---|---|
| V2 | 18 (ACL) | 1.6 (ACL) | — | — | 0.6 | 19 |
| V23-008 | 10 (ACL) | 1.8 (ACL) | — | — | 0.6 | 18 |
| V23-014 | 6 (ACL) | 1.0 (ACL) | — | — | 1.0 | — |
| V59 | 24 (CRF)/ 10 (ACL) | 1.5 (CRF)/ 2.1 (ACL) | 8.1 | 31.7 | 1.24 | 38 (ACL)/ 28 (CRF) |
| V62 | — | — | 2.3 | 15.7 | 1.62 | — |
| V76 | 13 (CRF) | 1.0 (CRF) | 0.58 | 4.23 | 1.63 | 11 |
| V78 | 16 | 1.6 | 0.60 | 0.00 | 1.36 | 16 |
| V79 | 12 | 1.4 | 1.8 | 0.9 | 1.41 | 13 |
| V79 (PLLA-PCL) | 37 | 1.3 | — | — | 1.21 | 1 |
| V80 | 12 | 0.4 | 0.00 | 0.00 | 0.91 | 8 |

TABLE 4B performance characteristics for scaffold types in TABLE 2

Figure 21:
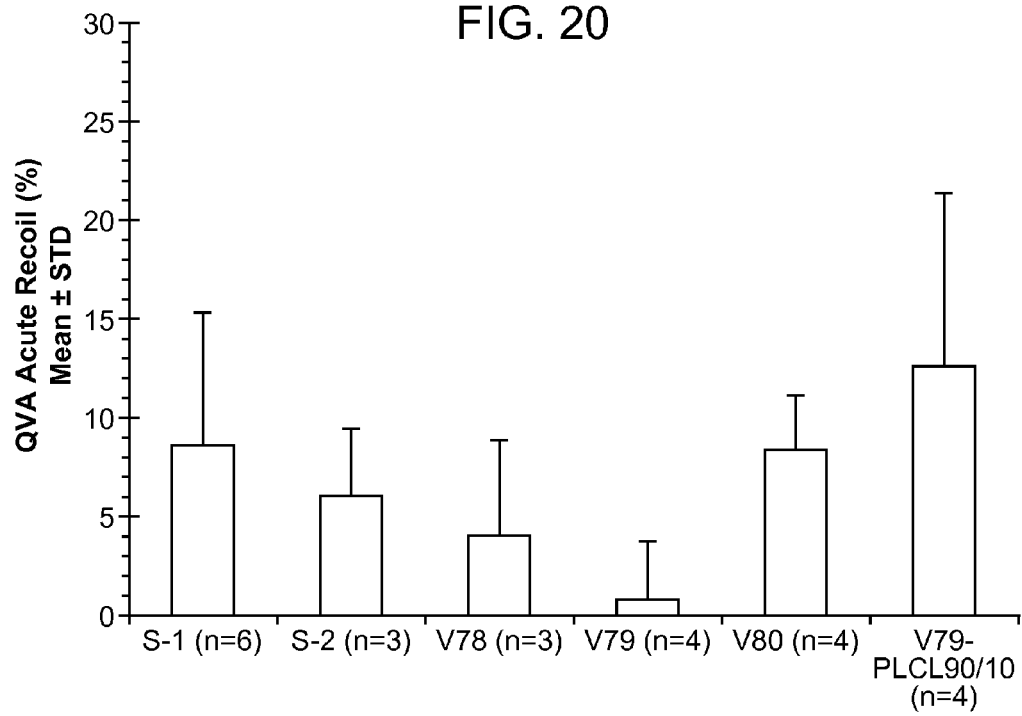
FIG. 21 compares the acute recoil percentage for several different scaffolds.

| Scaffold Type | Acute recoil (%) FIGS. 12 and 21 | Recoil after 7 days (%) | Crush Recovery (18% crush) | Crush Recovery (33% crush) | Crush Recovery (50% crush) | Crush Recovery (67% crush) |
|---|---|---|---|---|---|---|
| V2 | 2.5 | | | | | |
| V23-008 | 4.4 | 3.6 | | | | |
| V23-014 | — | | | | | |

TABLE 4B-continued performance characteristics for scaffold types in TABLE 2

| Scaffold Type | Acute recoil (%) FIGS. 12 and 21 | Recoil after 7 days (%) | Crush Recovery (18% crush) | Crush Recovery (33% crush) | Crush Recovery (50% crush) | Crush Recovery (67% crush) |
|---|---|---|---|---|---|---|
| V59 | 3.2 | 3.8 | 99% | 94% | 86% | 82.5% |
| V62 | 3.8 | 7.67 | 99% | 96% | 91% | 82.5% |
| V76 | 3.3 | 6.11 | 99% | 96% | 91% | 75% |
| V78 | 3.0 | 5.91 | | | | |
| V79 | 3.4 | 6.33 | 98% | 94% | 83.4% | 75.3% |
| V79 (PLLA-PCL) | 3.0 | | 98% | 94% | 88% | 76% |
| V80 | 3.6 | 7.52 | 98% | 94% | 87% | 83% |

Referring to FIG. 16, the high number of crests provides the V80 scaffolds with unique flexibility and as a result is more fracture resistant than the other scaffolds when axial fatigue properties are evaluated by six-month simulated walking. The low fracture rate is also well translated and shows good correlation with in-vivo testing, as demonstrated in FIG. 17.

Because the V80 scaffold has more struts/scaffold-length than the other scaffolds, the struts need to be less wide and as a result the radial strength of the V80 scaffold is significantly lower than other two-link scaffolds (V76-V79).

Radial strength and stiffness are sometimes thought of as synonymous to scaffolding properties. According to this view, the V80 design would therefore appear to have a poor ability to maintain patency as compared to the other scaffolds. However, as seen in FIG. 18 the V80 scaffold shows a significantly lower late loss than the other more radially stiff scaffolds, even where the fracture percentages and/or rates are similar, e.g., V79 compared with V80. As shown in FIG. 19 the lower late loss shows statistical significance at 28 days relative to the other scaffold designs.

While not wishing to be tied to any particular theory, the explanation for why the V80 design shows significantly lower late loss is believed to lie in the higher number of, or density of struts. With a greater number of struts the V80 provides more scaffolding (higher surface area and more support). In particular, when a strut is fracturing there is still significant support to push back the vessel. This aspect of the V80 may be understood in the following manner. For an equal number of fractures, there is a lower percentage of non-functioning strut-crown structures to the total number of strut-crown structures. Thus, while there may be an equal number of fractures as in other designs, the V80 is capable of providing a better or more consistent scaffolding over the vessel luminal surface because it has a larger number of intact crown-strut structures for every failed crown-strut structure.

FIG. 20 shows that the V23-014 scaffold, which has a lower number of crowns but a higher wall thickness, produced a lower percentage of stenosis than the V80. This may be explained by an increase in the fatigue life of the scaffold struts (i.e., fewer fractures) since the thicker wall lowers the average stress for a strut for the same loading conditions.

FIG. 21 shows acute recoil for the V78, V79, V80 and V79 scaffolds.

Figure 22:
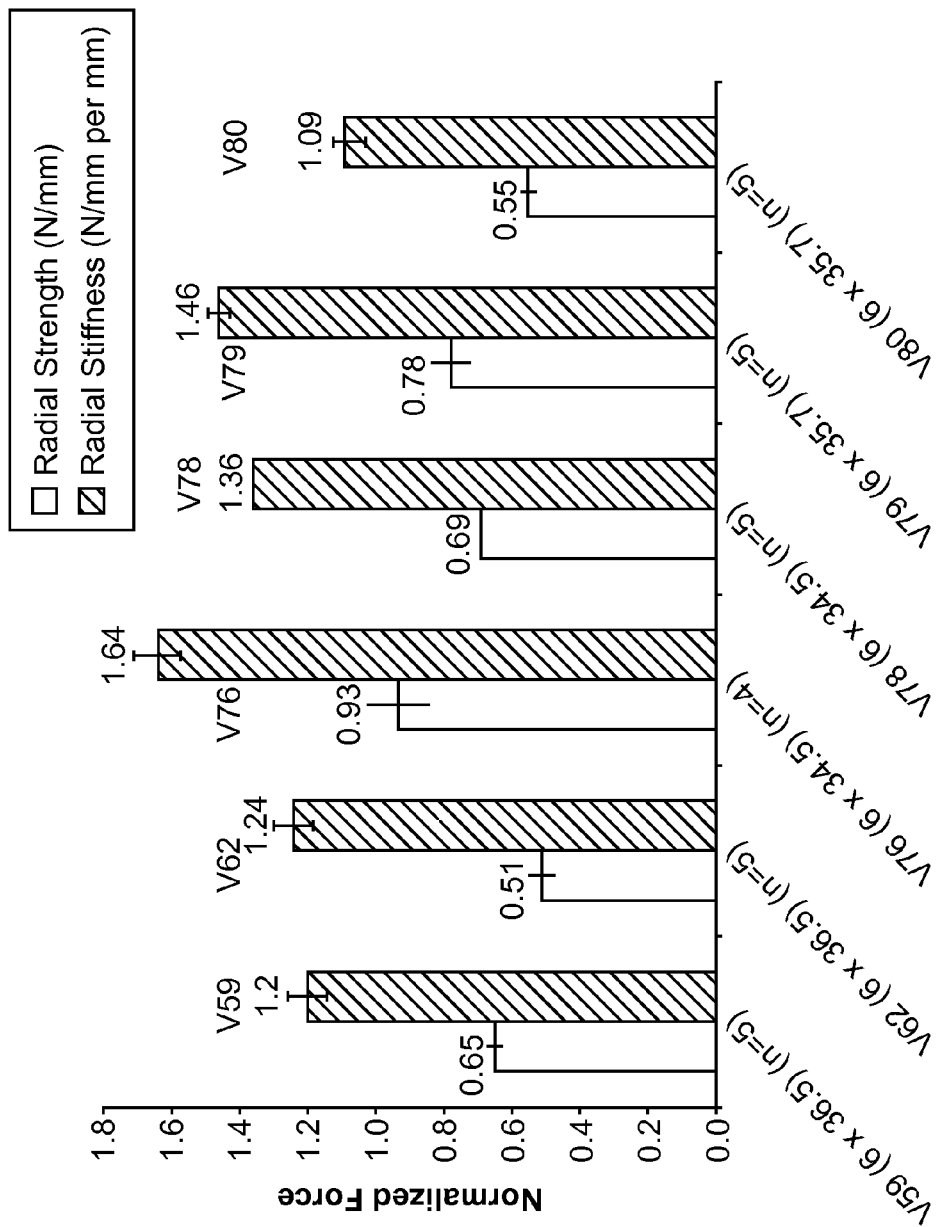
FIG. 22 shows the radial strength (N/mm) and radial stiffness (N/mm per mm) for the V59, V62, V76, V78, V79 and V80 scaffolds.

FIG. 22 shows the radial strength (N/mm) and radial stiffness (N/mm per mm) for the V59, V62, V76, V78, V79 and V80 scaffolds.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A medical device, comprising:
    a balloon;
    a scaffold that was cut from a tube comprising PLLA, wherein the tube has a ratio of diameter to wall thickness of between 20-40;
    wherein the scaffold forms a network of rings interconnected by links, including
        at least 8 crests and 8 troughs per ring,
        a first ring,
        a second ring adjacent the first ring, and
        at most 2 links connecting the first ring to the second ring;
    wherein the scaffold is crimped to the balloon by plastic deformation of the scaffold such that the scaffold has a crimped state;
    wherein the scaffold has a post-dilation diameter when plastically deformed from the crimped state by inflation of the balloon and the scaffold attains over 80% of the post-dilation diameter after being crushed by an amount equal to over 50% of the post-dilation diameter; and
    wherein the scaffold rings comprise struts and at least 90% of the struts are intact after a six-month simulated walking test.

2. The device of claim 1, wherein the balloon has a nominal inflation diameter of between 5 to 8 mm and the tube is a biaxially-expanded tube having at least a 6 mm outer diameter.

3. The device of claim 1, wherein the scaffold is made from a polymer composition comprising PLLA.

4. The device of claim 1, wherein polymer chains of the crimped scaffold are aligned substantially in a radial direction resulting from a radial expansion of between about 400% and 450% and axial expansion of between 150% and 200%.

5. The device of claim 1, wherein the scaffold attains about 80% of the post-dilation diameter after being crushed by an amount equal to over 60% of the post-dilation diameter.

6. The device of claim 1, wherein the scaffold has 8, 9 or 12 crowns per ring.

7. A medical device, comprising:
    a scaffold formed from a radially expanded polymer tube and configured for being crimped to a balloon by plastic deformation of the scaffold wherein the plastically deformed scaffold has a crimped state;

the scaffold having a pre-crimp diameter and a wall thickness, wherein a ratio of the pre-crimp diameter to the wall thickness is between 20-40, and wherein the scaffold forms a network of rings interconnected by links, including at least 8 crests and 8 troughs per ring, a first ring, a second ring adjacent the first ring, and at most 2 links connecting the first ring to the second ring;

wherein the scaffold has a post-dilation diameter when plastically deformed from the crimped state by inflation of the balloon and the scaffold attains over 80% of the post-dilation diameter after being crushed by an amount equal to over 50% of the post-dilation diameter.

8. The medical device of claim 7, wherein the scaffold has 8 crests and 8 troughs per ring, or 12 crests and 12 troughs per ring, each ring having a plurality of U crowns, Y crowns and W crowns, the rings further including a third ring adjacent the second ring, and a fourth ring adjacent the third ring, the first ring is connected to the second ring by two links, each of which being connected to the first ring at a W crown and the second ring at a Y crown and such that there are an equal number of U crowns on each side of the W crown of the first ring and each side of the Y crown of the second ring, the second ring is connected to the third ring by two links, each of which being connected to the second ring at a W crown and the third ring at a Y crown and such that there are an equal number of U crowns on each side of the W crown of the second ring and each side of the Y crown of the third ring, the third ring is connected to the fourth ring by two links, each of which being connected to the third ring at a W crown and the fourth ring at a Y crown and such that there are an equal number of U crowns on each side of the W crown of the third first ring and each side of the Y crown of the fourth ring.

9. The medical device of claim 8, wherein each of the links has a longitudinal axis and extends parallel to a longitudinal axis of the scaffold, and wherein each of the links connecting the first ring to the second ring is co-linear with a respective one of the links connecting the third ring to the fourth ring.

\* \* \* \* \*